US012805999B2

(12) United States Patent
Thyden et al.

(10) Patent No.: US 12,805,999 B2
(45) Date of Patent: Nov. 24, 2026

(54) ADJUSTABLE INSERTIONAL ACHILLES RECONSTRUCTION WITH COLLAGEN IMPLANT AUGMENTATION

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Michael Thyden, Billerica, MA (US); Stephen A. Santangelo, Sturbridge, MA (US)

(73) Assignees: Smith & Nephew, Inc.; Smith & Nephew Orthopaedics AG, Zug (CH); Smith & Nephew Asia Pacific Pte. Limited, Singapore (SG)

(*) Notice: Subject to any disclaimer, the term of this patent is extended or adjusted under 35 U.S.C. 154(b) by 1038 days.

(21) Appl. No.: 17/734,536

(22) Filed: May 2, 2022

(65) Prior Publication Data

US 2022/0346938 A1 Nov. 3, 2022

Related U.S. Application Data

(60) Provisional application No. 63/275,310, filed on Nov. 3, 2021, provisional application No. 63/246,988, filed (Continued)

(51) Int. Cl.
*A61F 2/08* (2006.01)

(52) U.S. Cl.
CPC .......... *A61F 2/0811* (2013.01); *A61F 2/0805* (2013.01); *A61F 2002/0829* (2013.01); (Continued)

(58) Field of Classification Search
CPC ............ A61F 2/0811; A61F 2002/0817; A61F 2002/0841; A61F 2002/0847; (Continued)

(56) References Cited

U.S. PATENT DOCUMENTS 5,733,307 A * 3/1998 Dinsdale ............ A61B 17/0401 606/232
7,172,595 B1 * 2/2007 Goble ................ A61B 17/1764 606/86 A (Continued)

FOREIGN PATENT DOCUMENTS

WO WO-2017075608 A1 * 5/2017 ............. A61B 17/00
WO 2021225858 A1 11/2021
WO WO-2024240871 A1 * 11/2024 ......... A61B 17/0401

OTHER PUBLICATIONS

"Advanced Healing Solutions," Smith and Nephew, pp. 1-8, printed 2020, Accessed May 25, 2021.

*Primary Examiner* — Alvin J Stewart
(74) *Attorney, Agent, or Firm* — Seager, Tufte & Wickhem LLP

(57) ABSTRACT

A kit and method for reconstructing an Achilles tendon may include a first anchor member, a first flexible member configured to engage the first anchor member, a second anchor member, a second flexible member configured to engage the second anchor member, a first adjustable anchor assembly including a first outer member and a first inner member configured to axially translate within a first lumen of the first outer member in response to rotation of the first inner member relative to the first outer member, a second adjustable anchor assembly include a second outer member and a second inner member configured to axially translate within a second lumen of the second outer member in response to rotation of the second inner member relative to the second outer member, and a collagen implant configured to engage a surface of the Achilles tendon.

6 Claims, 34 Drawing Sheets

Related U.S. Application Data on Sep. 22, 2021, provisional application No. 63/183,183, filed on May 3, 2021.

(52) U.S. Cl.
CPC ................. *A61F 2002/0852* (2013.01); *A61F 2002/0888* (2013.01)

(58) Field of Classification Search
CPC ...... A61F 2002/0852; A61F 2002/0858; A61F 2002/0864; A61F 2002/0888
See application file for complete search history.

(56) References Cited

U.S. PATENT DOCUMENTS

| | | | | |
|---|---|---|---|---|
| 8,012,174 | B2 | 9/2011 | ElAttrache et al. | |
| 8,231,653 | B2 | 7/2012 | Dreyfuss | |
| 8,419,794 | B2 | 4/2013 | ElAttrache et al. | |
| 8,702,754 | B2 * | 4/2014 | DiMatteo | A61B 17/0401 606/232 |
| 8,771,351 | B2 | 7/2014 | ElAttrache et al. | |
| 9,308,080 | B2 | 4/2016 | Housman et al. | |
| 9,345,471 | B2 | 5/2016 | Sullivan | |
| 9,386,977 | B2 * | 7/2016 | Lunn | A61B 17/0401 |
| 9,393,103 | B2 | 7/2016 | Van Kampen et al. | |
| 9,393,104 | B2 | 7/2016 | Kampen et al. | |
| 9,615,821 | B2 | 4/2017 | Sullivan | |
| 9,936,939 | B2 * | 4/2018 | Nguyen | A61B 17/0401 |
| 10,123,866 | B2 | 11/2018 | Van Kampen et al. | |
| 10,172,606 | B2 | 1/2019 | Sullivan et al. | |
| 10,188,378 | B2 * | 1/2019 | Lunn | A61B 17/0401 |
| 10,368,855 | B2 | 8/2019 | Burkhart | |
| 10,582,920 | B2 | 3/2020 | Lunn et al. | |
| 10,595,983 | B1 * | 3/2020 | Ferguson | A61B 17/06166 |
| 10,617,406 | B2 * | 4/2020 | Housman | A61B 17/0401 |
| 10,702,260 | B2 | 7/2020 | Sengun et al. | |
| 10,743,855 | B2 | 8/2020 | Nguyen et al. | |
| 10,743,981 | B2 * | 8/2020 | McCarty, III | A61F 2/0811 |
| 10,864,072 | B2 | 12/2020 | Van Kampen et al. | |
| 2002/0161401 | A1 * | 10/2002 | Steiner | A61B 17/0401 606/232 |
| 2003/0204193 | A1 | 10/2003 | Gabriel et al. | |
| 2007/0191849 | A1 | 8/2007 | ElAttrache et al. | |
| 2009/0112270 | A1 * | 4/2009 | Lunn | A61B 17/0401 606/301 |
| 2010/0069958 | A1 * | 3/2010 | Sullivan | A61B 17/0642 606/232 |
| 2010/0249833 | A1 | 9/2010 | Dreyfuss | |
| 2011/0112576 | A1 * | 5/2011 | Nguyen | A61B 17/0401 606/232 |
| 2013/0144310 | A1 * | 6/2013 | Gordon | A61B 17/0487 606/139 |
| 2013/0165972 | A1 | 6/2013 | Sullivan | |
| 2013/0345747 | A1 | 12/2013 | Dreyfuss | |
| 2013/0345750 | A1 | 12/2013 | Sullivan | |
| 2014/0309668 | A1 * | 10/2014 | Sullivan | A61B 17/0642 606/151 |
| 2015/0142024 | A1 * | 5/2015 | Arai | A61F 2/0811 606/151 |
| 2017/0105716 | A1 | 4/2017 | Burkhart | |
| 2017/0209135 | A1 | 7/2017 | Sullivan et al. | |
| 2018/0185133 | A1 * | 7/2018 | Dooney, Jr. | A61F 2/08 |
| 2020/0100890 | A1 * | 4/2020 | Hamilton | A61F 2/0811 |
| 2020/0170634 | A1 * | 6/2020 | Burkhart | A61F 2/0811 |
| 2020/0170783 | A1 * | 6/2020 | Adams | A61B 17/3423 |
| 2020/0197155 | A1 * | 6/2020 | Tsai | A61B 17/0401 |
| 2021/0022725 | A1 * | 1/2021 | Burkhart | A61B 17/0401 |
| 2021/0251741 | A1 * | 8/2021 | Bonner | A61F 2/08 |
| 2024/0108325 | A1 * | 4/2024 | Cook | A61B 17/0401 |
| 2025/0000506 | A1 * | 1/2025 | Vanderlaan | A61B 17/0466 |
| 2025/0107795 | A1 * | 4/2025 | Bowman | A61F 2/0811 |

* cited by examiner

ADJUSTABLE INSERTIONAL ACHILLES RECONSTRUCTION WITH COLLAGEN IMPLANT AUGMENTATION

CROSS REFERENCE TO RELATED APPLICATION

This application claims the benefit of U.S. Patent Application Ser. No. 63/183,183 filed on May 3, 2021, U.S. Patent Application Ser. No. 63/246,988 filed on Sep. 22, 2021 and U.S. Patent Application Ser. No. 63/275,310 filed Nov. 3, 2021, the disclosures of which are incorporated herein by reference.

TECHNICAL FIELD

The present disclosure pertains to medical devices and methods for using medical devices. More particularly, the present disclosure pertains to a method of insertional Achilles reconstruction.

BACKGROUND

Standard insertional Achilles reconstruction procedures are done by detaching the Achilles from the calcaneus, removing Haglund's deformity from the calcaneus, and then reattaching the Achilles to the calcaneus. To reattach the Achilles to the calcaneus, four knotless suture anchors are commonly used with suture tape. The superior row of anchors may pinch and/or secure suture tape between the anchor(s) and the bone via interference fit. Then the inferior row of anchors is inserted into the bone, which anchors also pinch and/or secure suture tape between the anchor(s) and the bone via interference fit. The tension of the construct must be estimated prior to insertion of the inferior row of anchors because after the distal or inferior row of anchors is inserted, the tension cannot be adjusted. There remains a need for improved devices and/or procedures that may permit greater adjustability and/or improved fit of the construct.

SUMMARY

In one example, a kit for reconstructing an Achilles tendon may comprise a first anchor member, a first flexible member configured to engage the first anchor member, a second anchor member, a second flexible member configured to engage the second anchor member, a first adjustable anchor assembly including a first outer member and a first inner member configured to axially translate within a first lumen of the first outer member in response to rotation of the first inner member relative to the first outer member, a second adjustable anchor assembly include a second outer member and a second inner member configured to axially translate within a second lumen of the second outer member in response to rotation of the second inner member relative to the second outer member, and a collagen implant configured to engage a surface of the Achilles tendon.

In addition or alternatively to any example described herein, the first inner member is threadably engaged with the first outer member.

In addition or alternatively to any example described herein, a first free end of the first flexible member and a first free end of the second flexible member are configured to engage the first adjustable anchor assembly.

In addition or alternatively to any example described herein, the first inner member configured to axially translate in a distal direction within the first lumen of the first outer member to lock the first free end of the first flexible member and the first free end of the second flexible member in position relative to the first adjustable anchor assembly in response to clockwise rotation of the first inner member relative to the first outer member.

In addition or alternatively to any example described herein, the second inner member is threadably engaged with the second outer member.

In addition or alternatively to any example described herein, a second free end of the first flexible member and a second free end of the second flexible member are configured to engage the second adjustable anchor assembly.

In addition or alternatively to any example described herein, the second inner member is configured to axially translate in a distal direction within the second lumen of the second outer member to lock the second free end of the first flexible member and the second free end of the second flexible member in position relative to the second adjustable anchor assembly in response to clockwise rotation of the second inner member relative to the second outer member.

In addition or alternatively to any example described herein, the first flexible member and the second flexible member are suture tapes.

In addition or alternatively to any example described herein, a method of reconstructing an Achilles tendon may comprise:

- exposing a bone beneath the Achilles tendon;
- inserting a first anchor member into the bone that was exposed to secure a medial portion of a first flexible member to the bone, wherein the first flexible member includes a first free end and a second free end opposite the first anchor member;
- inserting a second anchor member into the bone that was exposed to secure a medial portion of a second flexible member to the bone, wherein the second flexible member includes a first free end and a second free end opposite the second anchor member; passing the first free end and the second free end of the first flexible member through the Achilles tendon at a first location;
- passing the first free end and the second free end of the second flexible member through the Achilles tendon at a second location;
- passing the first free end of the first flexible member and the first free end of the second flexible member through a through hole formed in a first outer member of a first adjustable anchor assembly, the first adjustable anchor assembly including a first inner member configured to axially translate within a first lumen of the first outer member in response to rotation of the first inner member relative to the first outer member;
- inserting the first adjustable anchor assembly into the bone at a first position inferior of the Achilles tendon;
- rotating the first inner member relative to the first outer member to secure the first flexible member and the second flexible member in position relative to the first adjustable anchor assembly;
- passing the second free end of the first flexible member and the second free end of the second flexible member through a through hole formed in a second outer member of a second adjustable anchor assembly, the second adjustable anchor assembly including a second inner member configured to axially translate within a second lumen of the second outer member in response to rotation of the second inner member relative to the second outer member;

inserting the second adjustable anchor assembly into the bone at a second position inferior of the Achilles tendon;

after inserting the second adjustable anchor assembly into the bone, applying tension to the second free end of the first flexible member;

after inserting the second adjustable anchor assembly into the bone, applying tension to the second free end of the second flexible member;

while maintaining tension of the second free end of the first flexible member and the second free end of the second flexible member, rotating the second inner member relative to the second outer member to secure the first flexible member and the second flexible member in position relative to the second adjustable anchor assembly; and securing a collagen implant in contact with an inferior end of the Achilles tendon.

In addition or alternatively to any example described herein, the method may comprise:

positioning the collagen implant at least partially over the inferior end of the Achilles tendon; and securing the collagen implant in position using the first flexible member and the second flexible member.

In addition or alternatively to any example described herein, wherein after passing the first free end and the second free end of the first flexible member through the Achilles tendon at the first location and passing the first free end and the second free end of the second flexible member through the Achilles tendon at the second location, and prior to positioning the collagen implant at least partially over the inferior end of the Achilles tendon:

passing the first free end and the second free end of the first flexible member through the collagen implant at a first site; and passing the first free end and the second free end of the second flexible member through the collagen implant at a second site.

In addition or alternatively to any example described herein, wherein securing the collagen implant in position using the first flexible member and the second flexible member includes holding the collagen implant against the inferior end of the Achilles tendon using the first flexible member and the second flexible member.

In addition or alternatively to any example described herein, the method may comprise:

positioning the collagen implant at least partially under the inferior end of the Achilles tendon; and securing the collagen implant in position using the first flexible member and the second flexible member.

In addition or alternatively to any example described herein, wherein prior to passing the first free end and the second free end of the first flexible member through the Achilles tendon at the first location and passing the first free end and the second free end of the second flexible member through the Achilles tendon at the second location:

passing the first free end and the second free end of the first flexible member through the collagen implant at a first site; and passing the first free end and the second free end of the second flexible member through the collagen implant at a second site.

In addition or alternatively to any example described herein, wherein securing the collagen implant in position using the first flexible member and the second flexible member includes holding the inferior end of the Achilles tendon against the collagen implant using the first flexible member and the second flexible member.

In addition or alternatively to any example described herein, the method may comprise:

rotating the first inner member relative to the first outer member to release the first flexible member and the second flexible member relative to the first adjustable anchor assembly;

adding tension to or releasing tension from the first free end of the first flexible member;

adding tension to or releasing tension from the first free end of the second flexible member; and while maintaining tension of the first free end of the first flexible member and the first free end of the second flexible member, rotating the first inner member relative to the first outer member to resecure the first flexible member and the second flexible member in position relative to the first adjustable anchor assembly.

In addition or alternatively to any example described herein, the method may comprise:

rotating the second inner member relative to the second outer member to release the first flexible member and the second flexible member relative to the second adjustable anchor assembly;

adding tension to or releasing tension from the free second end of the first flexible member;

adding tension to or releasing tension from the free second end of the second flexible member; and while maintaining tension of the second free end of the first flexible member and the second free end of the second flexible member, rotating the second inner member relative to the second outer member to resecure the first flexible member and the second flexible member in position relative to the second adjustable anchor assembly.

In addition or alternatively to any example described herein, the medial portion of the first flexible member is translatable relative to the first anchor member.

In addition or alternatively to any example described herein, the medial portion of the second flexible member is translatable relative to the second anchor member.

In addition or alternatively to any example described herein, a method of reconstructing an Achilles tendon may comprise:

exposing a bone beneath the Achilles tendon;

inserting a first anchor member into the bone that was exposed, wherein a first length of flexible member extends away from the first anchor member and a second length of flexible member extends away from the first anchor member;

inserting a second anchor member into the bone that was exposed, wherein a first length of flexible member extends away from the second anchor member and a second length of flexible member extends away from the second anchor member;

passing the first and second lengths of flexible member extending from the first anchor member through the Achilles tendon at a first location;

passing the first and second lengths of flexible member extending from the second anchor member through the Achilles tendon at a second location;

passing the first length of flexible member extending from the first anchor member and the first length of flexible member extending from the second anchor member through a through hole formed in a first outer member of a first adjustable anchor assembly, the first adjustable anchor assembly including a first inner member configured to axially translate within a first lumen of the first outer member in response to rotation of the first inner member relative to the first outer member;

inserting the first adjustable anchor assembly into the bone at a first position inferior of the Achilles tendon;

after inserting the first adjustable anchor assembly into the bone, applying tension to the first length of flexible member extending from the first anchor member;

after inserting the first adjustable anchor assembly into the bone, applying tension to the first length of flexible member extending from the second anchor member;

while maintaining tension of the first length of flexible member extending from the first anchor member and the first length of flexible member extending from the second anchor member, rotating the first inner member relative to the first outer member to secure the first length of flexible member extending from the first anchor member and the first length of flexible member extending from the second anchor member in position relative to the first adjustable anchor assembly;

passing the second length of flexible member extending from the first anchor member and the second length of flexible member extending from the second anchor member through a through hole formed in a second outer member of a second adjustable anchor assembly, the second adjustable anchor assembly including a second inner member configured to axially translate within a second lumen of the second outer member in response to rotation of the second inner member relative to the second outer member;

inserting the second adjustable anchor assembly into the bone at a second position inferior of the Achilles tendon;

after inserting the second adjustable anchor assembly into the bone, applying tension to the second length of flexible member extending from the first anchor member;

after inserting the second adjustable anchor assembly into the bone, applying tension to the second length of flexible member extending from the second anchor member;

while maintaining tension of the second length of flexible member extending from the first anchor member and the second length of flexible member extending from the second anchor member, rotating the second inner member relative to the second outer member to secure the second length of flexible member extending from the first anchor member and the second length of flexible member extending from the second anchor member in position relative to the second adjustable anchor assembly; and securing a collagen implant in contact with an inferior end of the Achilles tendon.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
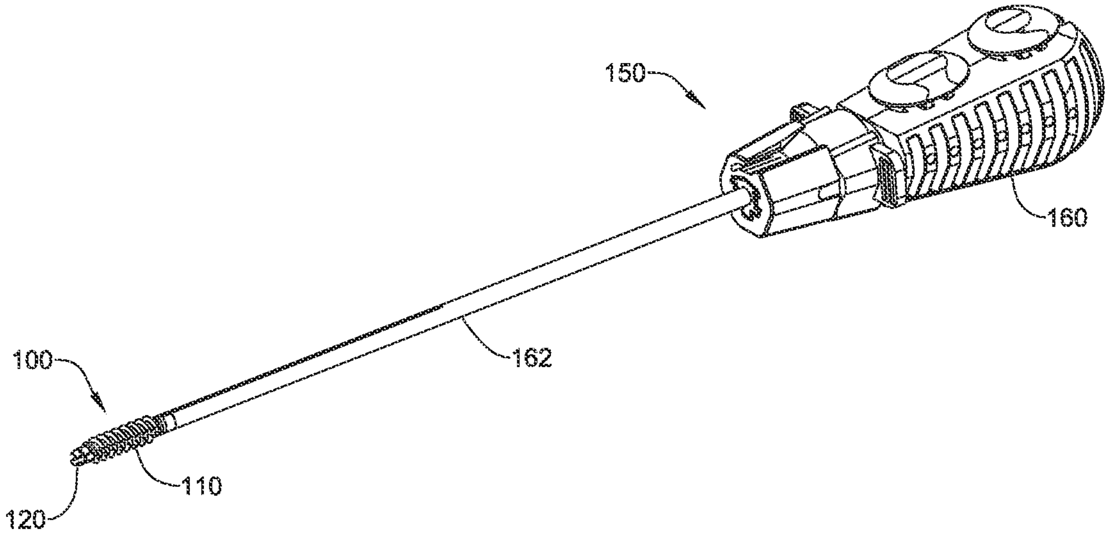
FIG. 1 illustrates aspects of an anchor member and a first tool for inserting the anchor member.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. The term "superior" may be understood to mean toward and/or closer to the head of a patient, while "inferior" may be understood to mean toward and/or closer to the feet of the patient. Other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It shall be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components, arrangements, and/or steps related to a method of reconstructing the Achilles tendon. It should be noted that in any given figure, some details and/or steps of the method may not be shown, or may be shown schematically, for simplicity. Additional details regarding some of the elements of the disclosure may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to features or elements may equally refer to all instances and quantities beyond one of said feature or element. As such, it will be understood that the following discussion may apply equally to any and/or all of the elements for which there are more than one within the disclosed structure, unless explicitly stated to the contrary. Additionally, not all instances of some elements or features may be shown in each figure for clarity.

FIG. 1 illustrates aspects of an anchor member 100 coupled to a delivery device 150. The delivery device 150 may include a handle 160 and a shaft 162 coupled to the handle 160. The shaft 162 may include a proximal end, a distal end, and a cannulation extending therein. In some embodiments, the shaft 162 may include markings along a length of the shaft 162. The anchor member 100 may include external threads 110 having an open helical form extending from a proximal end to a distal end of the anchor member 100. The anchor member 100 may include a suture bridge 120 disposed at the distal end of the anchor member 100. The suture bridge 120 may include a first base, a second base, and a recess disposed between the first base and the second base. The recess may extend toward the proximal end of the anchor member 100. The recess may be deep enough to permit a suture or a suture tape extending therethrough to slide around and/or relative to the suture bridge 120 when the first base and/or the second base is engaged against a surface (e.g., a bottom of a hole, etc.). In at least some embodiments, the recess may be concave. Other configurations are also contemplated. The anchor member 100 may include a plurality of runners extending axially along an interior of the anchor member 100. In a delivery configuration, the anchor member 100 may be engaged with a distal portion of the shaft 162 of the delivery device 150. The delivery device 150 may be configured to rotate the anchor member 100 relative to bone to drive the anchor member 100 into the bone using the external threads 110.

Figure 2:
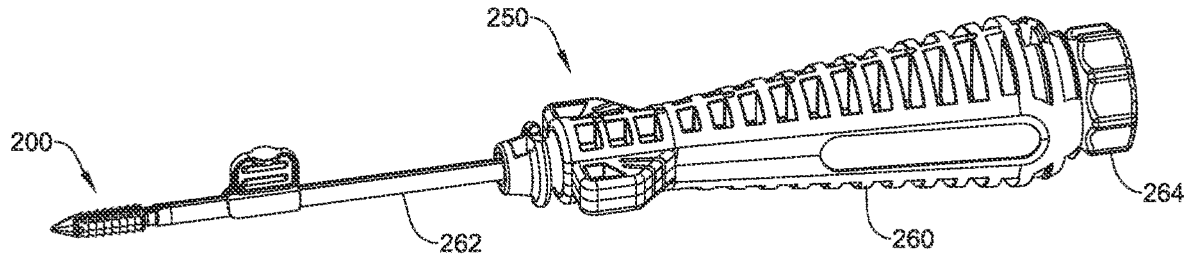
FIG. 2 illustrates aspects of an anchoring assembly and a second tool for inserting the anchoring assembly.
Figure 3:
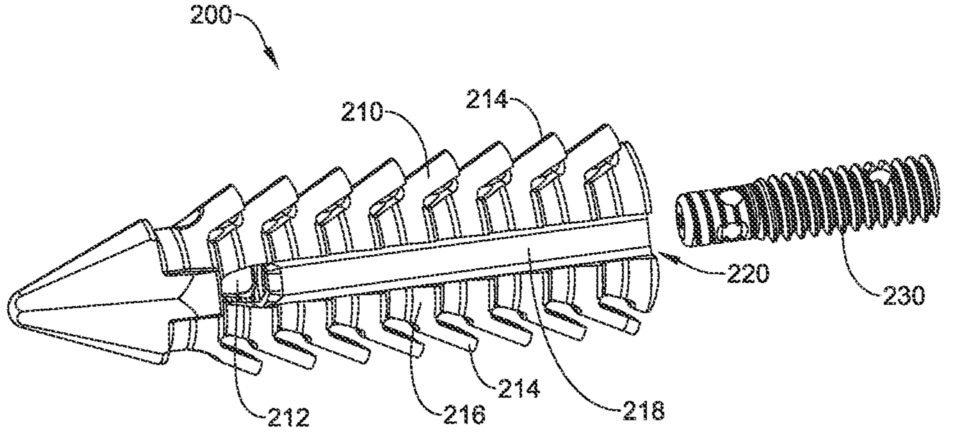
FIG. 3 illustrates aspects of the anchoring assembly of FIG. 2.

FIGS. 2-3 illustrate aspects of an adjustable anchor assembly 200 and a delivery device 250. The adjustable anchor assembly 200 may be releasably couplable to the delivery device 250. The adjustable anchor assembly 200 may include an outer member 210 defining a lumen 220 and an opening to the lumen 220 proximate a proximal end of the outer member 210. An inner member 230 may be configured to move within the lumen 220 relative to the outer member 210. In some embodiments, the inner member 230 may be threadably engaged with the outer member 210. The inner member 230 may be configured to axially translate within the lumen 220 of the outer member 210 in response to rotation of the inner member 230 relative to the outer member 210. In some embodiments, clockwise rotation of the inner member 230 relative to the outer member 210 may axially translate the inner member 230 distally within the lumen 220 of the outer member 210. In some embodiments, counterclockwise rotation of the inner member 230 relative to the outer member 210 may axially translate the inner member 230 proximally within the lumen 220 of the outer member 210. Other configurations are also contemplated.

As seen in FIG. 3, the outer member 210 may include a through hole 212 formed transversely to a central longitudinal axis of the outer member 210. The through hole 212 may communicate with the lumen 220 of the outer member 210. In some embodiments, the inner member 230 may be configured to obstruct the through hole 212 to secure a flexible member (e.g., a suture, a suture tape, etc.) relative to the adjustable anchor assembly 200 and/or the outer member 210. In some embodiments, the lumen 220 may have a closed distal end. In some embodiments, the inner member 230 may be configured to axially translate distally within the lumen 220 secure the flexible member between a distal end of the inner member 230 and the closed distal end of the lumen 220. In some embodiments, the inner member 230 may be configured to axially translate proximally within the lumen 220 release the flexible member relative to the adjustable anchor assembly 200.

The outer member 210 may include a plurality of wings 214 extending radially outward and proximally from a body portion 216 of the outer member 210. The plurality of wings 214 may be configured to secure the outer member 210 within a hole formed in a bone or other structure, thereby preventing the outer member 210 from pulling out of and/or being removed from the hole formed in the bone or other structure. In some embodiments, the body portion 216 of the outer member 210 may include a plurality of longitudinal slots 218 formed therein. The plurality of longitudinal slots 218 may face and/or open radially outward from the body portion 216. The plurality of longitudinal slots 218 may be adjacent to and/or in communication with the through hole 212. In some embodiments, the plurality of longitudinal slots 218 may include a first longitudinal slot and a second longitudinal slot disposed opposite the first longitudinal slot relative to the central longitudinal axis of the outer member 210. In some embodiments, the plurality of longitudinal slots 218 and/or the through hole 212 may be configured to slidably receive the flexible member therein such that the flexible member is slidable and/or translatable relative to the outer member 210 when the inner member 230 does not obstruct the through hole 212. The plurality of longitudinal slots 218 may be deep enough that when the outer member 210 is disposed within the hole formed in the bone or other structure, the flexible member is slidable and/or translatable between and/or relative to the outer member 210 and the bone when the inner member 230 does not obstruct the through hole 212.

Returning to FIG. 2, the delivery device 250 may include a handle 260 and a shaft 262 extending distally from the handle 260. The shaft 262 may include an inner shaft member and an outer shaft member. The inner shaft member may be rotatable and/or axially slidable relative to the outer shaft member. The outer shaft member of the shaft 262 may include a plurality of prongs at and/or adjacent a distal end of the outer shaft member of the shaft 262. The plurality of prongs may be configured to slidably engage with the plurality of longitudinal slots 218 of the outer member 210 of the adjustable anchor assembly 200 to prevent relative rotation between the outer member 210 and the outer shaft member of the shaft 262. The delivery device 250 may include a knob 264 coupled to a proximal end of the inner shaft member of the shaft 262. In some embodiments, the knob 264 may be configured to rotate relative to the handle 260. In at least some embodiments, the knob 264 may be fixedly attached to the proximal end of the inner shaft member of the shaft 262. A distal end portion of the inner shaft member may be configured to slidably engage with a cannulation extending axially within the inner member 230 of the adjustable anchor assembly 200. The inner shaft member may be non-rotatable relative to the inner member 230 when the inner shaft member is engaged with the cannulation and/or the inner member 230. As such, rotation of the knob 264 relative to the handle 260 may rotate the inner member 230 of the adjustable anchor assembly 200 relative to the outer member 210 of the adjustable anchor assembly 200.

Figure 4:
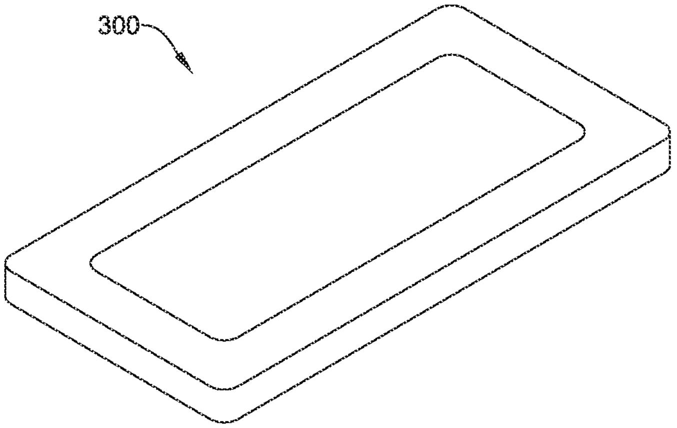
FIG. 4 illustrates aspects of an example collagen implant for use in Achilles reconstruction surgery.

FIG. 4 illustrates a collagen implant 300 for use in reconstruction of an Achilles tendon of a patient. The collagen implant 300 may comprise a tissue matrix configured to engage with and/or directly contact the Achilles tendon. In some embodiments, the collagen implant 300 may include collagen type I, although other forms of collagen (e.g., types II, III, IV, V, IX, or X) may be used and/or may be included and/or mixed with collagen type I. In some embodiments, the collagen implant 300 may have a thickness of about 5 millimeters or less, about 4 millimeters or less, about 3 millimeters or less, about 2 millimeters or less, or another suitable thickness. Preferably, the collagen implant 300 has a thickness of about 3 millimeters or less. In some embodiments, the collagen implant 300 may include bioactive components configured to stimulate a healing response within the patient. In some embodiments, the composition of the collagen implant 300 may be varied and/or optimized to promote a desired healing response. In some embodiments, the collagen implant 300 may be coated and/or impregnated with a therapeutic substance configured to promote or inhibit a particular response. The collagen implant 300 may increase healing potential, may shorten the length of time of the rehabilitation process, may stimulate natural healing response, may accelerate healing of tissue, and/or may induce new tendon-like tissue growth.

Figure 5:
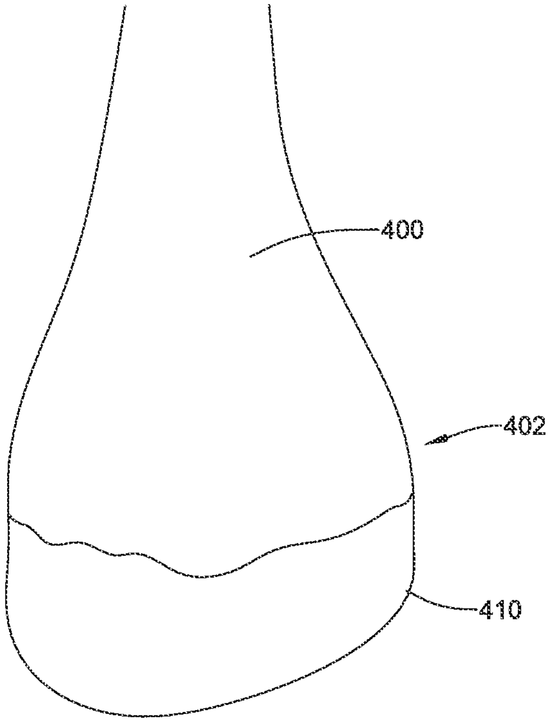
FIGS. 5-7 illustrate aspects a method of reconstructing an Achilles tendon related to preparing the bone.
Figure 6:
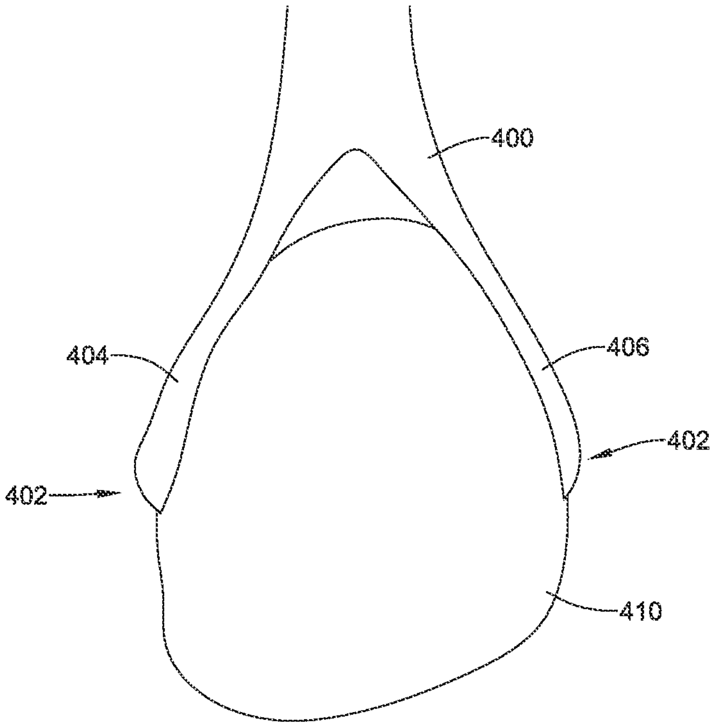

A method of reconstructing an Achilles tendon may include one or more of the following described steps, features, and/or elements. FIG. 5 illustrates an Achilles tendon 400 which may be in need of reconstruction. The Achilles tendon 400 is shown attached to a bone 410 at its inferior end 402. The bone 410 may be the calcaneus or heel bone, as would be understood by the skilled person. For ease of understanding, skin, muscle tissue, and other bones are not shown. After the Achilles tendon 400 is accessed through the patient's skin, the Achilles tendon 400 may be split from the inferior end 402 in a superior direction generally along a medial line of the Achilles tendon 400 to form a first lateral portion 404 and a second lateral portion 406 opposite the first lateral portion 404 relative to the medial line of the Achilles tendon 400, as seen in FIG. 6. The method may include exposing a surface of the bone 410 beneath the Achilles tendon 400. For example, the first lateral portion 404 and the second lateral portion 406 may be spread apart laterally and/or away from the medial line to expose the surface of the bone 410 (e.g., the calcaneus) beneath the Achilles tendon 400.

Figure 7:
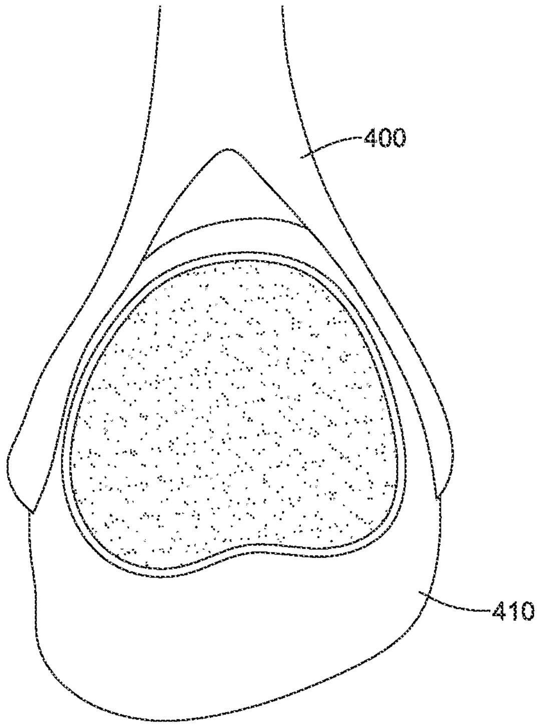
Figure 8:
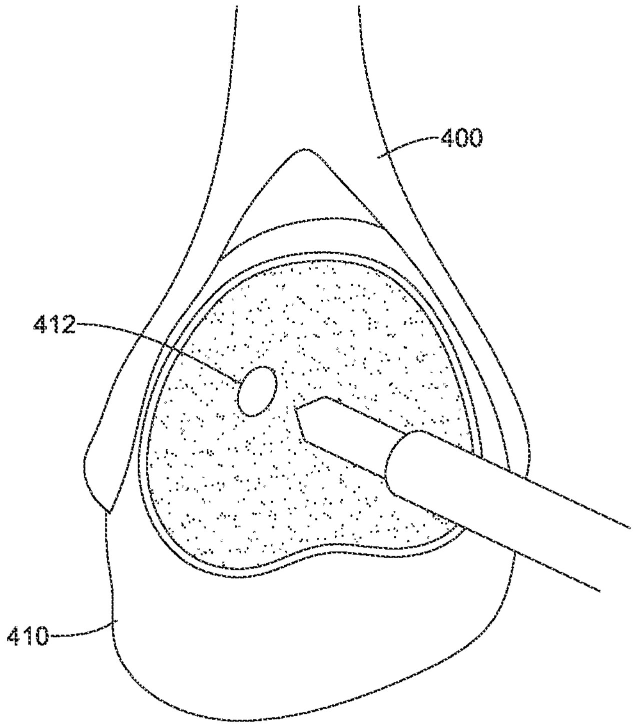
FIGS. 8-13 illustrate aspects of the method of reconstructing the Achilles tendon related to inserting first and second anchor members into the bone.
Figure 9:
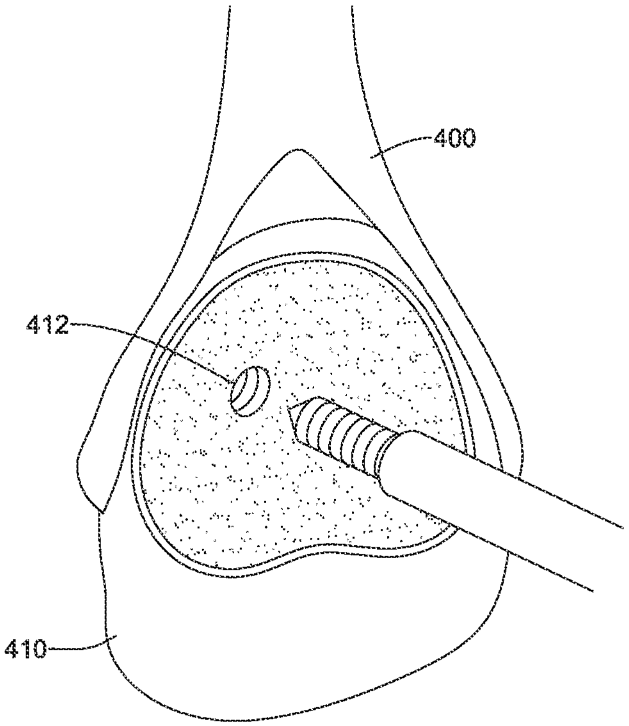
Figure 10:
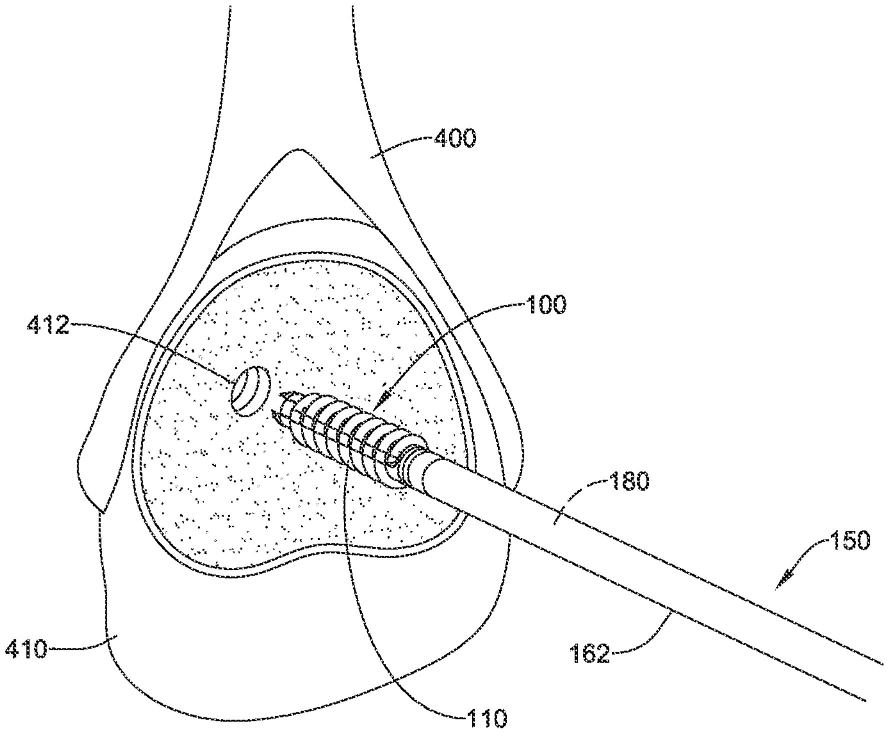

In at least some embodiments, the method may include resecting a portion of the bone 410 (e.g., the calcaneus) and/or a portion of the surface of the bone 410 that was exposed to remove Haglund's deformity, as seen in FIG. 7. In some embodiments, no resection may be necessary. Next, the method may include drilling a first hole 412 in the surface of the bone 410 that was exposed and/or resected to a depth sufficient to accept a first anchor member 100 flush with and/or recessed below the surface of the bone 410, as shown in FIG. 8. Then, the method may include tapping and/or threading the first hole 412 to form internal threads therein, as seen in FIG. 9, wherein the internal threads are configured to matingly receive the external threads 110 of the first anchor member 100. In some embodiments, the drilling and/or tapping steps may be skipped—for example, if the first anchor member 100 is configured to self-tap and/or screw directly into the bone 410. Other configurations are also contemplated. In some embodiments, the method may include aligning the first anchor member 100 with the first hole 412 with and/or using a first delivery device 150, as seen in FIG. 10. A first flexible member 180 may be engaged with the first anchor member 100 and may extend within the shaft 162 of the first delivery device 150.

Figure 11:
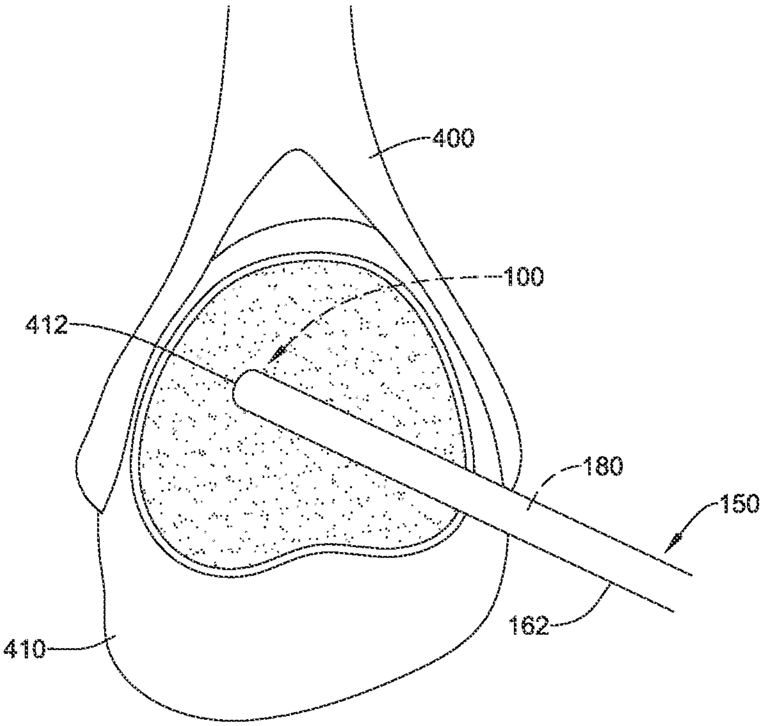
Figure 12:
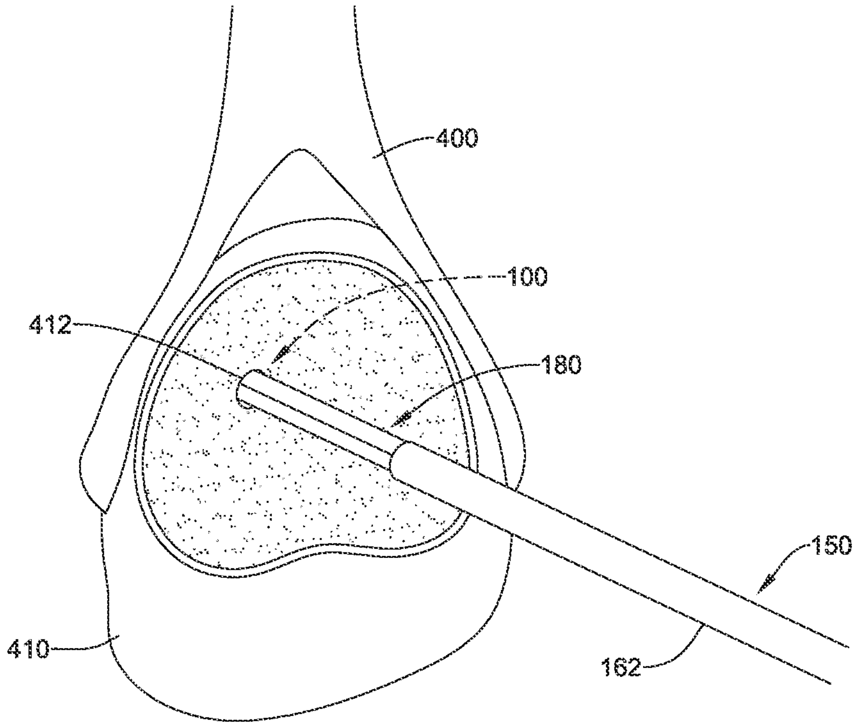

The method may include inserting the first anchor member 100 into the surface of the bone 410 that was exposed and/or resected using the first delivery device 150, as seen in FIG. 11, until a proximal end of the first anchor member 100 is flush with and/or recessed below the surface of the bone 410 that was exposed and/or resected. In at least some embodiments, inserting the first anchor member 100 into the surface of the bone 410 that was exposed and/or resected may include rotating the first anchor member 100 relative to the bone 410. In some embodiments, the handle 160 (e.g., FIG. 1) and/or the shaft 162 of the first delivery device 150 may be rotated relative to the bone 410 to drive, screw, and/or insert the first anchor member 100 into the first hole 412. The shaft 162 and/or the delivery device 150 may be disengaged from the first anchor member 100 by proximally retracting the shaft 162 and/or the delivery device 150, without rotation, from the first anchor member 100, thereby leaving the first anchor member 100 secured within the first hole 412 formed in the bone 410, as seen in FIG. 12. In some embodiments, the method may include inserting the first anchor member 100 into the surface of the bone 410 that was exposed and/or resected to secure a medial portion of the first flexible member 180 to the bone 410. In some embodiments, the first flexible member 180 may include and/or may be a suture, a filament, or other similar elements. In some embodiments, the first flexible member 180 may include and/or may be a suture tape. A suture tape may include a flattened shape and the suture tape may have a width and a thickness, wherein the width is greater than the thickness.

Figure 13:
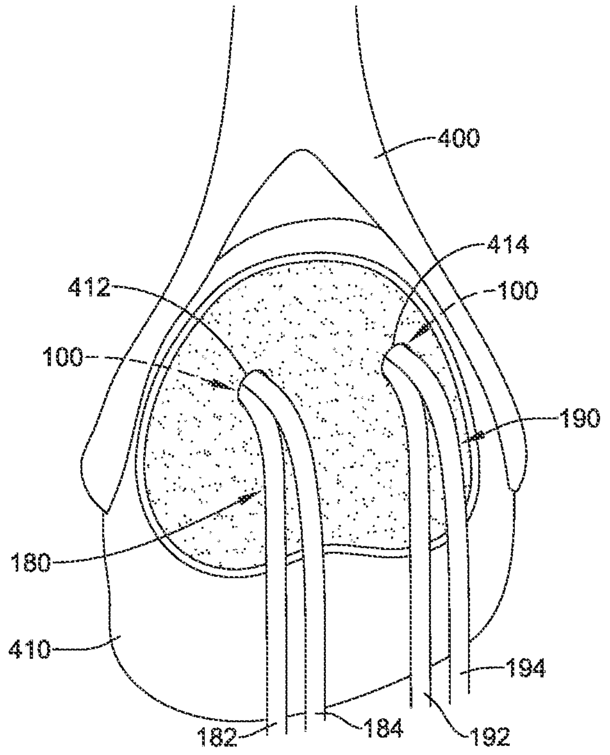

The method may include substantially repeating the steps related to inserting the first anchor member 100 shown in FIGS. 8-12 to insert a second anchor member 100, as generally shown in FIG. 13. For example, the method may include drilling a second hole 414 in the surface of the bone 410 that was exposed and/or resected to a depth sufficient to accept a second anchor member 100 flush with and/or recessed below the surface of the bone 410. Then, the method may include tapping and/or threading the second hole 414 to form internal threads therein, wherein the internal threads are configured to matingly receive the external threads 110 of the second anchor member 100. In some embodiments, the drilling and/or tapping steps may be skipped—for example, if the second anchor member 100 is configured to self-tap and/or screw directly into the bone 410. Other configurations are also contemplated. In some embodiments, the method may include aligning the second anchor member 100 with the second hole 414 with and/or using a second delivery device 150.

The method may include inserting the second anchor member 100 into the surface of the bone 410 that was exposed and/or resected using the second delivery device 150, until a proximal end of the second anchor member 100 is flush with and/or recessed below the surface of the bone 410 that was exposed and/or resected. A second flexible member may be engaged with the second anchor member 100 and may extend within the shaft 162 of the second delivery device 150. In at least some embodiments, inserting the second anchor member 100 into the surface of the bone 410 that was exposed and/or resected may include rotating the second anchor member 100 relative to the bone 410. In some embodiments, the handle 160 (e.g., FIG. 1) and/or the shaft 162 of the second delivery device 150 may be rotated relative to the bone 410 to drive, screw, and/or insert the second anchor member 100 into the second hole 414. The shaft 162 and/or the delivery device 150 may be disengaged from the second anchor member 100 by proximally retracting the shaft 162 and/or the delivery device 150, without rotation, from the second anchor member 100, thereby leaving the second anchor member 100 secured within the second hole 414 formed in the bone 410, as seen in FIG. 13. In some embodiments, the method may include inserting the second anchor member 100 into the surface of the bone 410 that was exposed and/or resected to secure a medial portion of a second flexible member 190 to the bone 410. In some embodiments, the second flexible member 190 may include and/or may be a suture, a filament, or other similar elements. In some embodiments, the second flexible member 190 may include and/or may be a suture tape, as described herein.

As may be seen in FIG. 13, the first flexible member 180 may include a first free end 182 and a second free end 184 opposite the first anchor member 100. For example, the first free end 182 may extend away from the first anchor member 100 and/or the medial portion of the first flexible member 180. Similarly, the second flexible member 190 may include a first free end 192 and a second free end 194 opposite the second anchor member 100. For example, the first free end 192 may extend away from the second anchor member 100 and/or the medial portion of the second flexible member 190.

Figure 14:
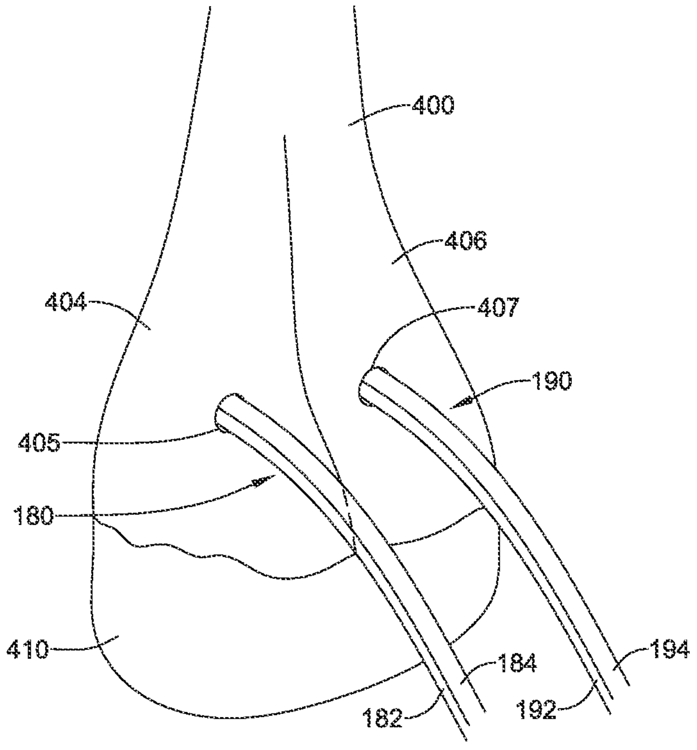
FIGS. 14-15 illustrate aspects of the method of reconstructing the Achilles tendon.

In some embodiments, the method may include passing the first free end 182 and the second free end 184 of the first flexible member 180 through the Achilles tendon 400 at a first location, as seen in FIG. 14. In some embodiments, the method may include passing the first free end 182 and the second free end 184 of the first flexible member 180 through the first lateral portion 404 of the Achilles tendon 400 at the first location. In some embodiments, the method may include forming a first opening 405 in the first lateral portion 404 of the Achilles tendon 400 at the first location. In some embodiments, the method may include passing the first free end 182 and the second free end 184 of the first flexible member 180 through the first opening 405 formed in the first lateral portion 404 of the Achilles tendon 400 at the first location. In some embodiments, the method may include passing the first free end 192 and the second free end 194 of the second flexible member 190 through the Achilles tendon 400 at a second location spaced apart from the first location, as seen in FIG. 14. In some embodiments, the method may include passing the first free end 192 and the second free end 194 of the second flexible member 190 through the second lateral portion 406 of the Achilles tendon 400 at the second location.

In some embodiments, the method may include forming a second opening 407 in the second lateral portion 406 of the Achilles tendon 400 at the second location. In some embodiments, the method may include passing the first free end 192 and the second free end 194 of the second flexible member 190 through the second opening 407 formed in the second lateral portion 406 of the Achilles tendon 400 at the second location. As will be appreciated, forming the first opening 405 and/or the second opening 407 in the Achilles tendon 400 may not be necessary in some embodiments. For example, in some embodiments, the first free end 182 and the second free end 184 of the first flexible member 180 and/or the first free end 192 and the second free end 194 of the second flexible member 190 may be passed through the Achilles tendon 400 using a needle or other guide element configured to penetrate the Achilles tendon 400 without a pre-formed opening disposed therein.

The method may include urging the first lateral portion 404 of the Achilles tendon 400 and the second lateral portion 406 of the Achilles tendon 400 toward each other such that the first lateral portion 404 of the Achilles tendon 400 is immediately adjacent to and/or comes into contact with the second lateral portion 406 of the Achilles tendon 400 in a closed position.

Figure 15:
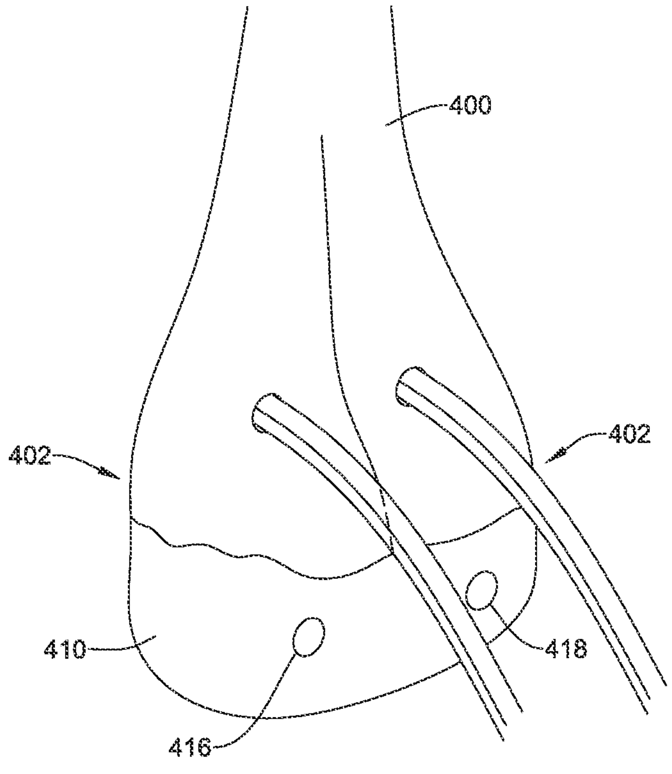

The method may include drilling a third hole 416 and a fourth hole 418 in the bone 410 inferior to the inferior end 402 of the Achilles tendon 400 in the closed position, as seen in FIG. 15. The third hole 416 and the fourth hole 418 may be spaced apart inferiorly from the inferior end 402 of the Achilles tendon 400 in the closed position. Since the first hole 412 and the second hole 414 are located beneath the Achilles tendon 400 in the closed position, the third hole 416 and the fourth hole 418 are also spaced apart inferiorly from the first hole 412 and the second hole 414 when the Achilles tendon 400 is in the closed position. The third hole 416 may be generally aligned in a superior-inferior direction with the first hole 412. The fourth hole 418 may be generally aligned in the superior-inferior direction with the second hole 414. The third hole 416 may be generally aligned laterally with the fourth hole 418. Other configurations are also contemplated.

Figure 16:
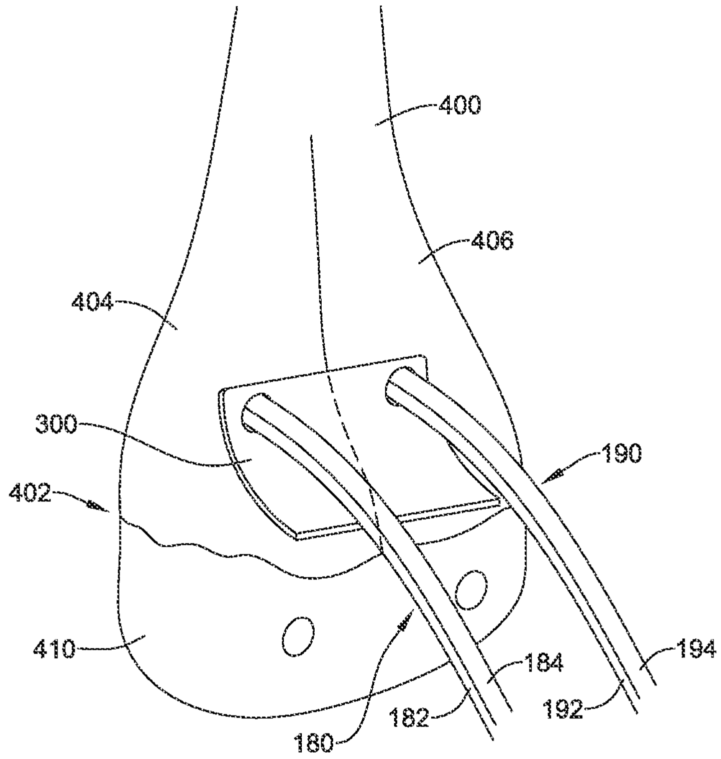
FIG. 16 illustrates aspects of a configuration using the collagen implant of FIG. 4 in the method of reconstructing the Achilles tendon.

In at least some embodiments, the method may include securing a collagen implant 300 in contact with the inferior end 402 of the Achilles tendon 400. In some embodiments, the method may include positioning the collagen implant 300 at least partially over the inferior end 402 of the Achilles tendon 400, and subsequently securing the collagen implant 300 in position using the first flexible member 180 and the second flexible member 190. In some embodiments, the method may include, after passing the first free end 182 and the second free end 184 of the first flexible member 180 through the first opening 405 formed in the first lateral portion 404 of the Achilles tendon 400 at the first location and passing the first free end 192 and the second free end 194 of the second flexible member 190 through the second opening 407 formed in the second lateral portion 406 of the Achilles tendon 400 at the second location, and prior to positioning the collagen implant 300 at least partially over the inferior end 402 of the Achilles tendon 400, passing the first free end 182 and the second free end 184 of the first flexible member 180 through the collagen implant 300 at a first site, and passing the first free end 192 and the second free end 194 of the second flexible member 190 through the collagen implant 300 at a second site spaced apart from the first site, as shown in FIG. 16.

In some embodiments, the method may include positioning the collagen implant 300 at least partially over the inferior end 402 of the Achilles tendon 400, and subsequently securing the collagen implant 300 in position using the first flexible member 180 and the second flexible member 190. In some embodiments, the method may include, after passing the first free end 182 and the second free end 184 of the first flexible member 180 through the first opening 405 formed in the first lateral portion 404 of the Achilles tendon 400 at the first location and passing the first free end 192 and the second free end 194 of the second flexible member 190 through the second opening 407 formed in the second lateral portion 406 of the Achilles tendon 400 at the second location, and prior to positioning the collagen implant 300 at least partially over the inferior end 402 of the Achilles tendon 400, passing the first free end 182 and the second free end 184 of the first flexible member 180 through a first hole formed in the collagen implant 300 at the first site, and passing the first free end 192 and the second free end 194 of the second flexible member 190 through a second hole formed in the collagen implant 300 at the second site. Other configurations are also contemplated.

In some embodiments, securing the collagen implant 300 in position using the first flexible member 180 and the second flexible member 190 may include holding the collagen implant 300 against a posterior facing portion of the inferior end 402 of the Achilles tendon 400 using the first flexible member 180 and the second flexible member 190, as described herein.

Figure 17:
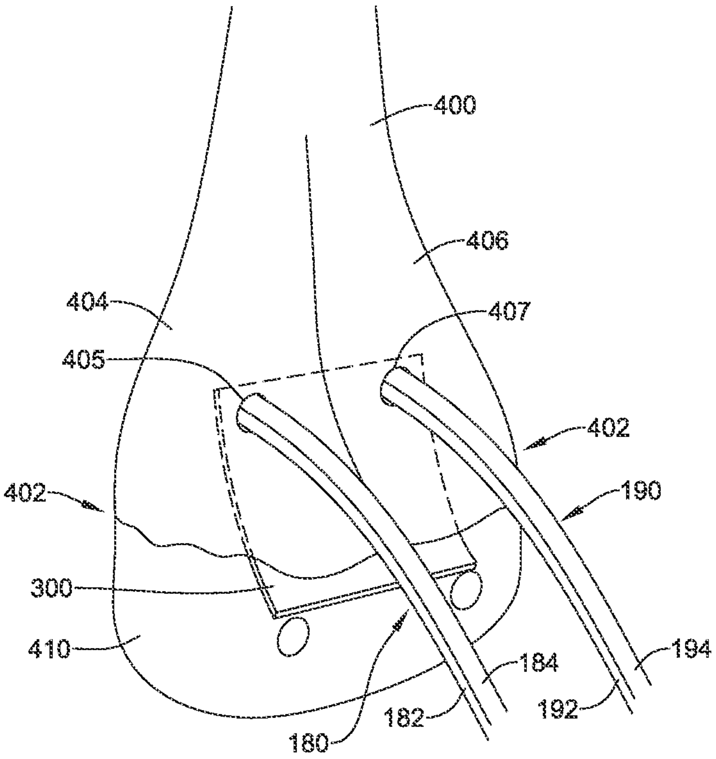
FIG. 17 illustrates aspects of an alternative configuration using the collagen implant of FIG. 4 in the method of reconstructing the Achilles tendon.

Alternatively, in some embodiments, the method may include positioning the collagen implant 300 at least partially under the inferior end 402 of the Achilles tendon 400, and subsequently securing the collagen implant 300 in position using the first flexible member 180 and the second flexible member 190. In some embodiments, the method may include, prior to passing the first free end 182 and the second free end 184 of the first flexible member 180 through the first opening 405 formed in the first lateral portion 404 of the Achilles tendon 400 at the first location and passing the first free end 192 and the second free end 194 of the second flexible member 190 through the second opening 407 formed in the second lateral portion 406 of the Achilles tendon 400 at the second location, passing the first free end 182 and the second free end 184 of the first flexible member 180 through the collagen implant 300 at the first site, and passing the first free end 192 and the second free end 194 of the second flexible member 190 through the collagen implant 300 at the second site, as shown in FIG. 17.

In some embodiments, the method may include positioning the collagen implant 300 at least partially under the inferior end 402 of the Achilles tendon 400, and subsequently securing the collagen implant 300 in position using the first flexible member 180 and the second flexible member 190. In some embodiments, the method may include, prior to passing the first free end 182 and the second free end 184 of the first flexible member 180 through the first opening 405 formed in the first lateral portion 404 of the Achilles tendon 400 at the first location and passing the first free end 192 and the second free end 194 of the second flexible member 190 through the second opening 407 formed in the second lateral portion 406 of the Achilles tendon 400 at the second location, passing the first free end 182 and the second free end 184 of the first flexible member 180 through a first hole formed in the collagen implant 300 at the first site, and passing the first free end 192 and the second free end 194 of the second flexible member 190 through a second hole formed in the collagen implant 300 at the second site. Other configurations are also contemplated.

In some embodiments, securing the collagen implant 300 in position using the first flexible member 180 and the second flexible member 190 may include holding an anterior facing portion of the inferior end 402 of the Achilles tendon 400 against the collagen implant 300 using the first flexible member 180 and the second flexible member 190.

Figure 18:
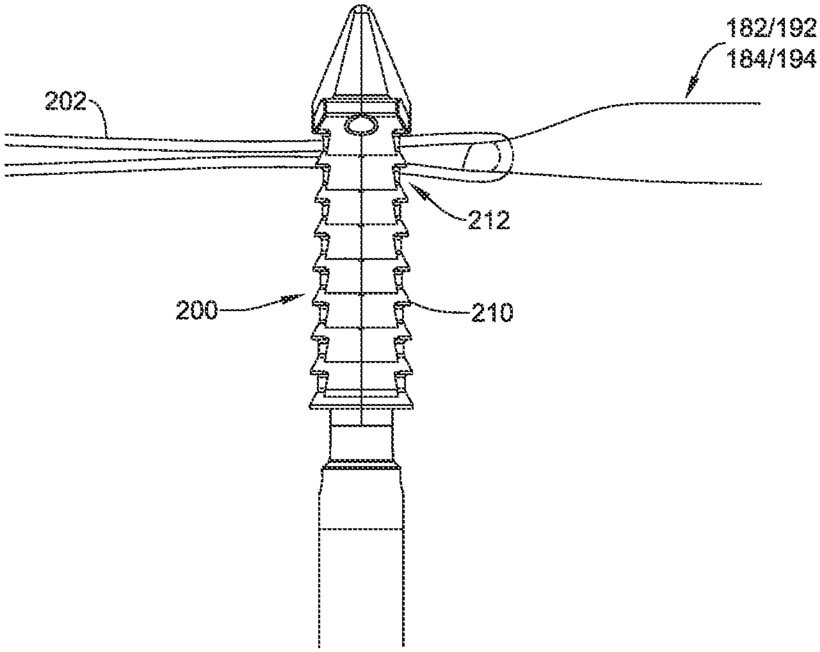
FIGS. 18-20 illustrate aspects of the method of reconstructing the Achilles tendon related to inserting a first anchoring assembly of FIGS. 2-3 into the bone.

The method may include passing the first free end 182 of the first flexible member 180 and the first free end 192 of the second flexible member 190 through a through hole 212 formed in a first outer member 210 of a first adjustable anchor assembly 200, as seen in FIG. 18. The first free end 182 of the first flexible member 180 and the first free end 192 of the second flexible member 190 may be configured to engage the first adjustable anchor assembly 200. The first adjustable anchor assembly 200 may include a first inner member 230 (e.g., FIG. 3) configured to axially translate within a first lumen 220 (e.g., FIG. 3) of the first outer member 210 in response to rotation of the first inner member 230 relative to the first outer member 210. The first inner member 230 may be threadably engaged with the first outer member 210. In some embodiments, a wire or a dedicated tool 202 may be used to guide, pull, and/or pass the first free end 182 of the first flexible member 180 and the first free end 192 of the second flexible member 190 through the through hole 212 of the first outer member 210 of the first adjustable anchor assembly 200. Other configurations are also contemplated.

Figure 19:
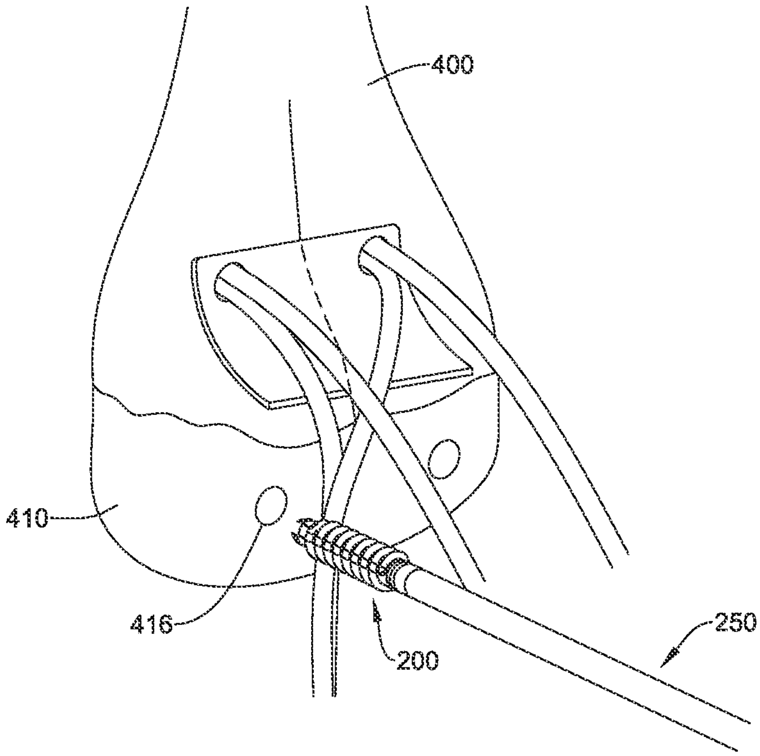
Figure 20:
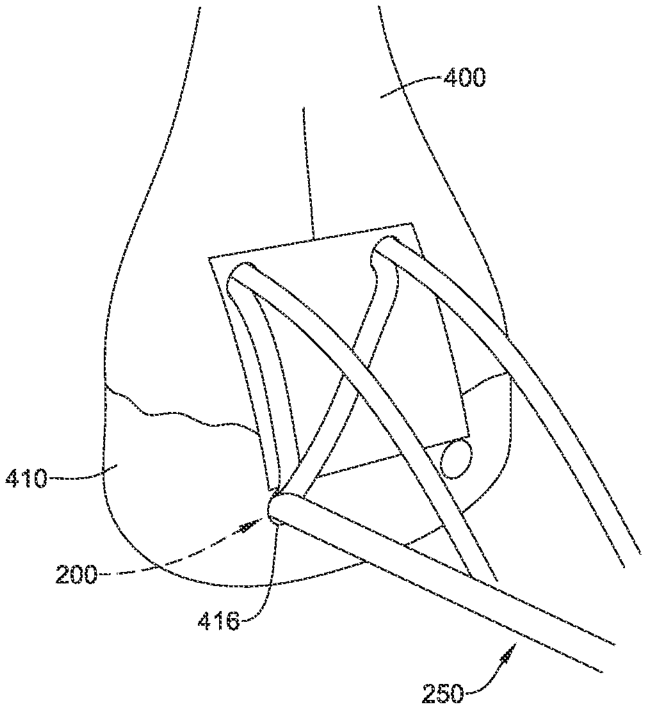

In some embodiments, the method may include aligning the first adjustable anchor assembly 200 with the third hole 416 formed in the bone 410 with and/or using a first delivery device 250, as seen in FIG. 19. The method may include inserting the first adjustable anchor assembly 200 into the third hole 416 formed in the bone 410 at a first position inferior of the Achilles tendon 400 until a proximal end of the first adjustable anchor assembly 200 and/or the first outer member 210 (e.g., FIGS. 2-3) is flush with and/or recessed below the surface of the bone 410, as seen in FIG. 20. In at least some embodiments, inserting the first adjustable anchor assembly 200 into the bone 410 may include tapping the handle 260 (e.g., FIG. 2) of the first delivery device 250 with a mallet or hammer to drive and/or insert the first adjustable anchor assembly 200 into the third hole 416 formed in the bone 410.

Figure 21:
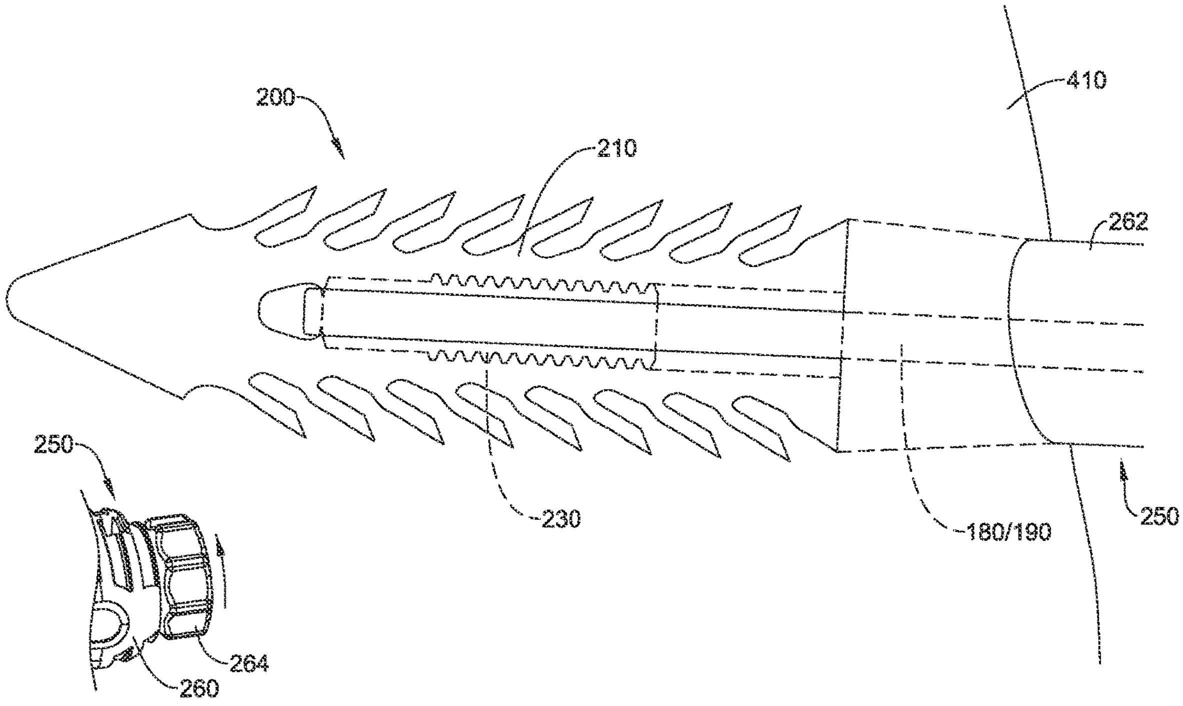
FIGS. 21-22 illustrate aspects of the method of reconstructing the Achilles tendon related to securing suture tapes relative to the first anchoring assembly.
Figure 22:
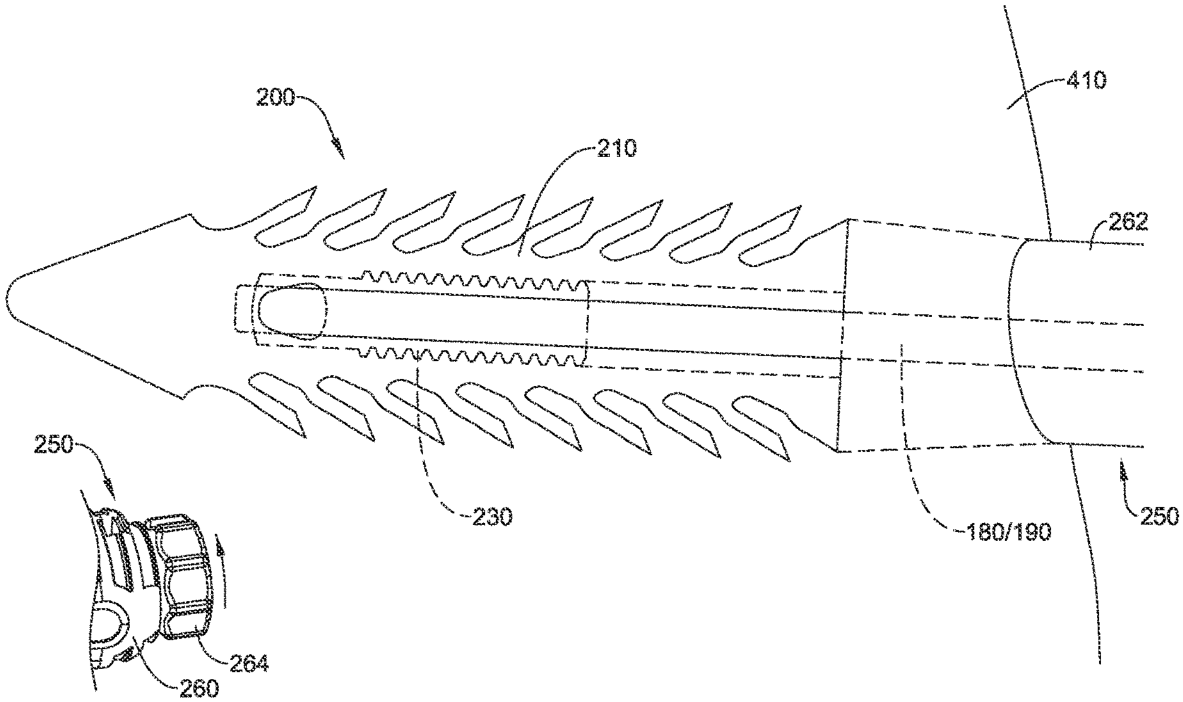

After inserting the first adjustable anchor assembly 200 into the third hole 416 formed in the bone 410, the method may include rotating the first inner member 230 of the first adjustable anchor assembly 200 relative to the first outer member 210 of the first adjustable anchor assembly 200 to axially translate the first inner member 230 in a distal direction within the first lumen 220 of the first outer member 210 to secure the first flexible member 180 and the second flexible member 190 in position relative to the first adjustable anchor assembly 200. The method may include rotating the knob 264 relative to the handle 260 to rotate the first inner member 230 relative to the first outer member 210 to axially translate the first inner member 230 within the first lumen 220 of the first outer member 210 to secure the first flexible member 180 and the second flexible member 190 in position relative to the first adjustable anchor assembly 200, as shown in FIGS. 21-22. For clarity, elements of the first adjustable anchor assembly 200 that would be outwardly visible if not disposed within the bone 410 are shown in solid lines, while other elements are shown in phantom. However, it will be understood that all elements of the first adjustable anchor assembly 200 are disposed within the bone 410 in FIGS. 21-22 and thus would not be outwardly visible. In at least some embodiments, the method may include rotating the knob 264 clockwise relative to the handle 260 to rotate the first inner member 230 relative to the first outer member 210 to axially translate the first inner member 230 within the first lumen 220 of the first outer member 210 to secure the first flexible member 180 and the second flexible member 190 in position relative to the first adjustable anchor assembly 200. In some embodiments, the first inner member 230 may be configured to axially translate in a distal direction within the first lumen 220 of the first outer member 210 to lock the first free end 182 of the first flexible member 180 and the first free end 192 of the second flexible member 190 in position relative to the first adjustable anchor assembly 200 in response to clockwise rotation of the first inner member 230 relative to the first outer member 210.

After securing the first flexible member 180 and the second flexible member 190 in position relative to the first adjustable anchor assembly 200, the shaft 262 and/or the first delivery device 250 may be disengaged from the first adjustable anchor assembly 200 by proximally retracting the shaft 262 and/or the first delivery device 250, without rotation, from the first adjustable anchor assembly 200, thereby leaving the first adjustable anchor assembly 200 secured within the third hole 416 formed in the bone 410.

The method may include passing the second free end 184 of the first flexible member 180 and the second free end 194 of the second flexible member 190 through a through hole 212 formed in a second outer member 210 of a second adjustable anchor assembly 200, as illustrated in FIG. 18. The second free end 184 of the first flexible member 180 and the second free end 194 of the second flexible member 190 may be configured to engage the second adjustable anchor assembly 200. The second adjustable anchor assembly 200 may include a second inner member 230 configured to axially translate within a second lumen 220 of the second outer member 210 in response to rotation of the second inner member 230 relative to the second outer member 210. The second inner member 230 may be threadably engaged with the second outer member 210. In some embodiments, a wire or a dedicated tool 202 may be used to guide, pull, and/or pass the second free end 184 of the first flexible member 180 and the second free end 194 of the second flexible member 190 through the through hole 212 of the second outer member 210 of the second adjustable anchor assembly 200. Other configurations are also contemplated.

Figure 23:
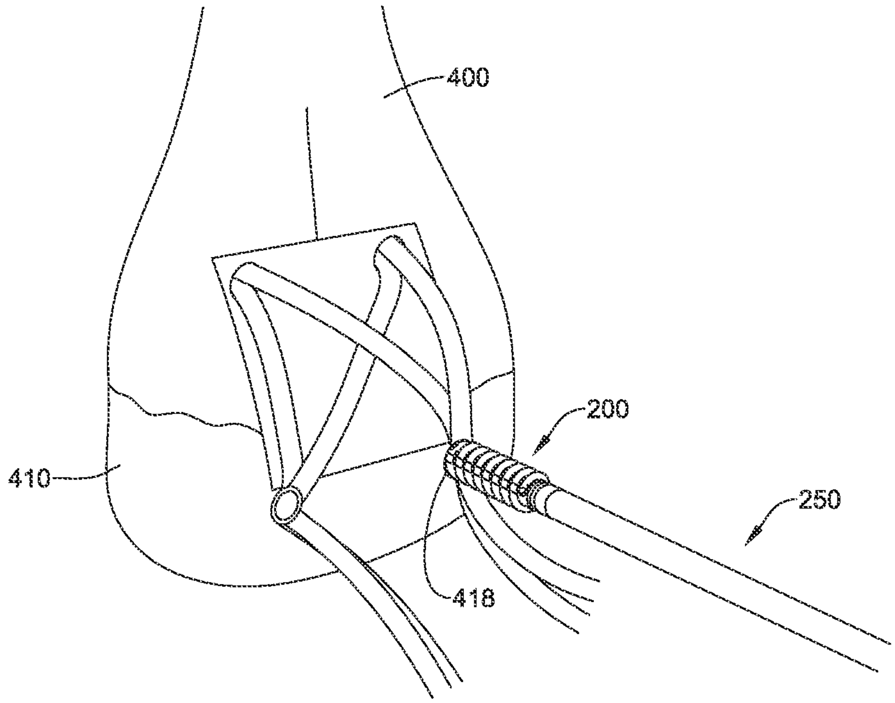
FIG. 23-24 illustrate aspects of the method of reconstructing the Achilles tendon related to inserting a second anchoring assembly of FIGS. 2-3 into the bone.
Figure 24:
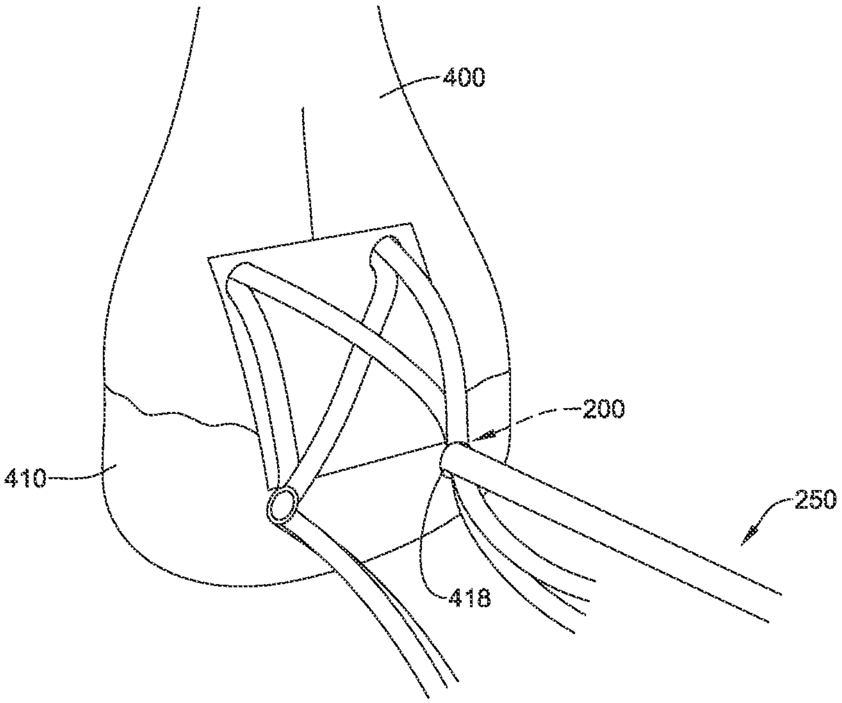

In some embodiments, the method may include aligning the second adjustable anchor assembly 200 with the fourth hole 418 with and/or using a second delivery device 250, as seen in FIG. 23. The method may include inserting the second adjustable anchor assembly 200 into the fourth hole 418 formed in the bone 410 at a second position inferior of the Achilles tendon 400 until a proximal end of the second adjustable anchor assembly 200 and/or the second outer member 210 (e.g., FIG. 3) is flush with and/or recessed below the surface of the bone 410, as seen in FIG. 24. In at least some embodiments, inserting the second adjustable anchor assembly 200 into the bone 410 may include tapping the handle 260 (e.g., FIG. 2) of the second delivery device 250 with a mallet or hammer to drive and/or insert the second adjustable anchor assembly 200 into the fourth hole 418 formed in the bone 410.

Figure 25:
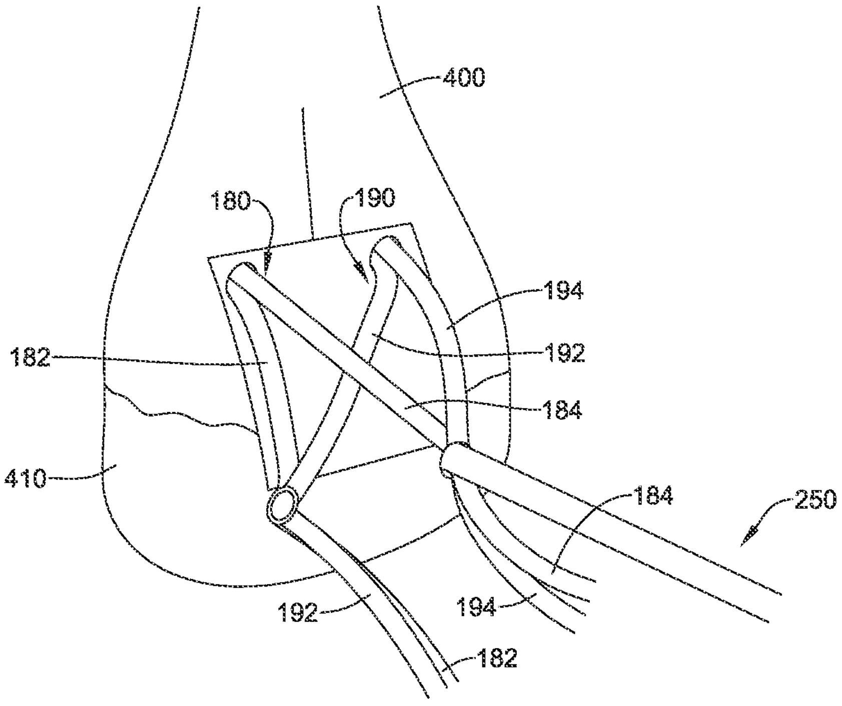
FIGS. 25-26 illustrate aspects of the method of reconstructing the Achilles tendon related to tightening the sutures tapes and securing the suture tapes relative to the second anchoring assembly.
Figure 26:
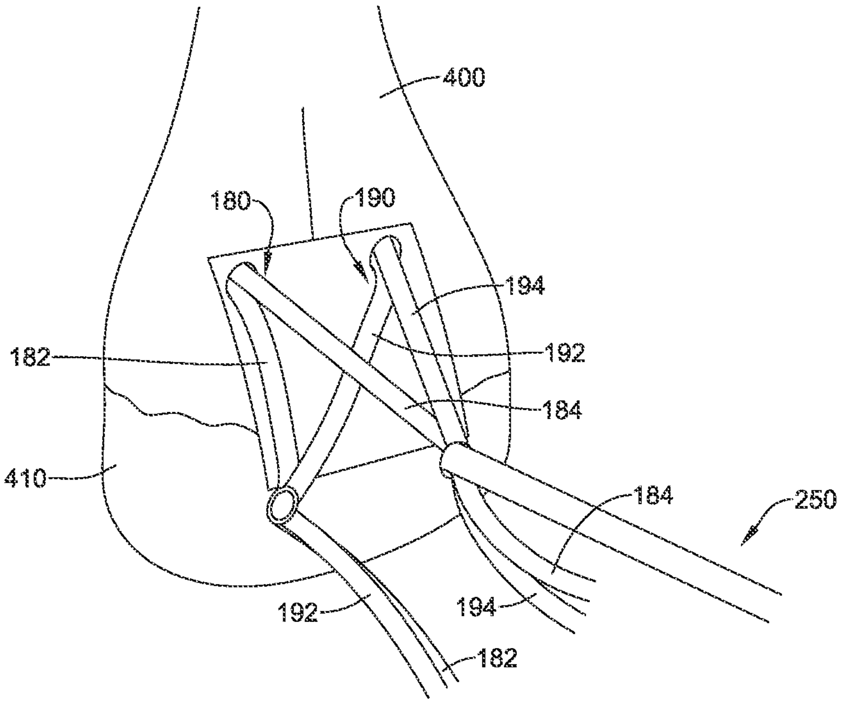

After inserting the second adjustable anchor assembly 200 into the fourth hole 418 formed in the bone 410, there may be slack or looseness in the first flexible member 180 and/or the second flexible member 190. After inserting the second adjustable anchor assembly 200 into the fourth hole 418 formed in the bone 410, the method may include applying tension to the second free end 184 of the first flexible member 180 and/or applying tension to the second free end 194 of the second flexible member 190, as seen in FIGS. 25-26. In at least some embodiments, the second free end 184 of the first flexible member 180 and the second free end 194 of the second flexible member 190 may be pulled and/or may have tension applied thereto individually and/or independently of each other.

In some embodiments, applying tension to the second free end 184 of the first flexible member 180 may cause the medial portion of the first flexible member 180 to slide and/or translate through and/or relative to the first anchor member 100 to remove slack within the first flexible member 180. In some embodiments, applying tension to the second free end 184 of the first flexible member 180 may cause the medial portion of the first flexible member 180 to slide and/or translate around and/or past the suture bridge 120 of the first anchor member 100 to remove slack within the first flexible member 180. In some embodiments, applying tension to the second free end 194 of the second flexible member 190 may cause the medial portion of the second flexible member 190 to slide and/or translate through and/or relative to the second anchor member 100 to remove slack within the second flexible member 190. In some embodiments, applying tension to the second free end 194 of the second flexible member 190 may cause the medial portion of the second flexible member 190 to slide and/or translate around and/or past the suture bridge 120 of the second anchor member 100 to remove slack within the second flexible member 190.

After applying tension to the second free end 184 of the first flexible member 180 and the second free end 194 of the second flexible member 190, the method may include rotating the second inner member 230 of the second adjustable anchor assembly 200 relative to the second outer member 210 of the second adjustable anchor assembly 200 to axially translate the second inner member 230 within the second lumen 220 of the second outer member 210 to secure the first flexible member 180 and the second flexible member 190 in position relative to the second adjustable anchor assembly 200. The method may include rotating the knob 264 relative to the handle 260 to rotate the second inner member 230 relative to the second outer member 210 to axially translate the second inner member 230 within the second lumen 220 of the second outer member 210 to secure the first flexible member 180 and the second flexible member 190 in position relative to the second adjustable anchor assembly 200, as shown in FIGS. 21-22. For clarity, elements of the second adjustable anchor assembly 200 that would be outwardly visible if not disposed within the bone 410 are shown in solid lines, while other elements are shown in phantom. However, it will be understood that all elements of the second adjustable anchor assembly 200 are disposed within the bone 410 in FIGS. 21-22 and thus would not be outwardly visible. In at least some embodiments, the method may include rotating the knob 264 clockwise relative to the handle 260 to rotate the second inner member 230 relative to the second outer member 210 to axially translate the second inner member 230 within the second lumen 220 of the second outer member 210 to secure the first flexible member 180 and the second flexible member 190 in position relative to the second adjustable anchor assembly 200. In some embodiments, the second inner member 230 may be configured to axially translate in a distal direction within the second lumen 220 of the second outer member 210 to lock the second free end 184 of the first flexible member 180 and the second free end 194 of the second flexible member 190 in position relative to the second adjustable anchor assembly 200 in response to clockwise rotation of the second inner member 230 relative to the second outer member 210.

Figure 27:
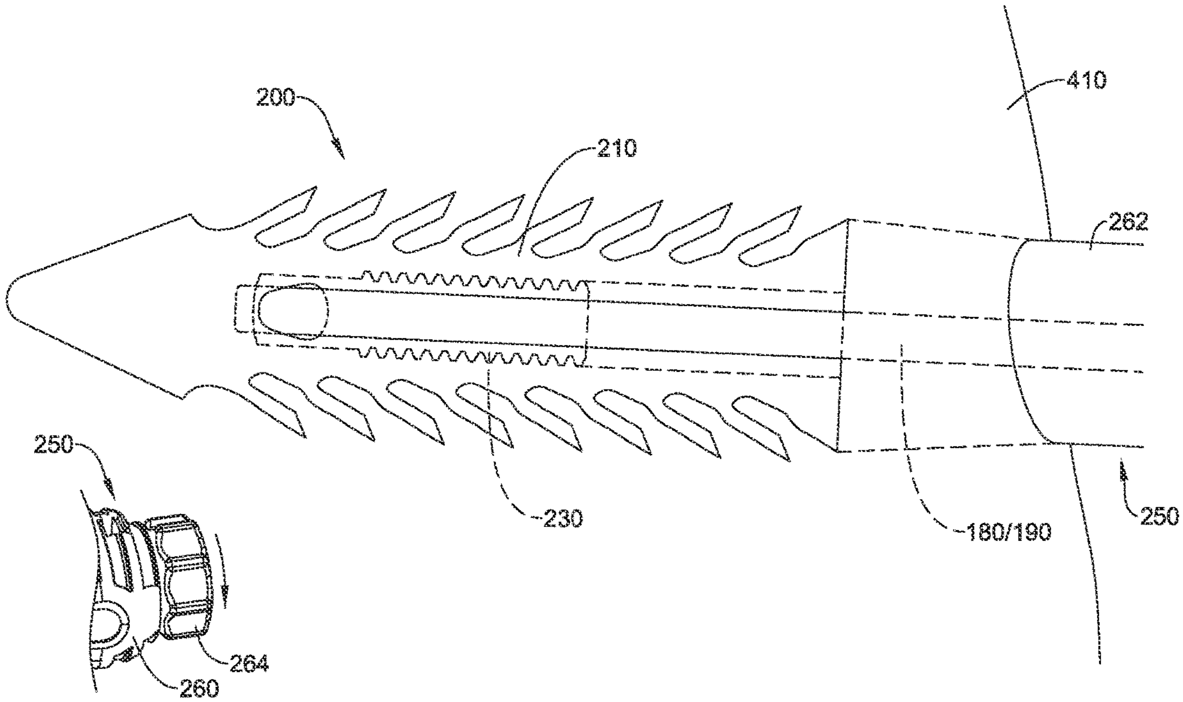
FIGS. 27-30 illustrates aspects of the method of reconstructing the Achilles tendon related to adjusting tension on the suture tapes after inserting the first and second anchoring assemblies.
Figure 28:
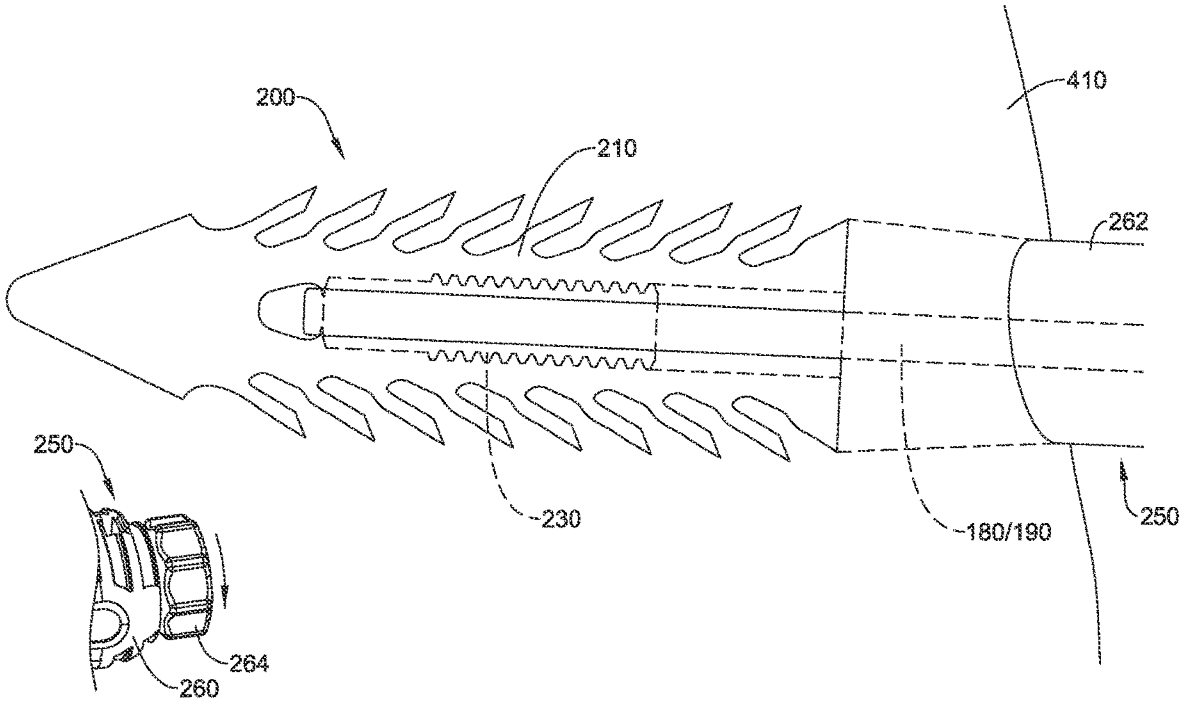

In some procedures, the tension on the first flexible member 180 and/or the second flexible member 190 may be more or less than desired. Accordingly, in some embodiments, the method may include rotating the second inner member 230 relative to the second outer member 210 to release the first flexible member 180 and the second flexible member 190 relative to the second adjustable anchor assembly 200. The method may include rotating the knob 264 relative to the handle 260 to rotate the second inner member 230 relative to the second outer member 210 to axially translate the second inner member 230 within the second outer member 210 to release the first flexible member 180 and the second flexible member 190 relative to the second adjustable anchor assembly 200, as shown in FIGS. 27-28. For clarity, elements of the second adjustable anchor assembly 200 that would be outwardly visible if not disposed within the bone 410 are shown in solid lines, while other elements are shown in phantom. However, it will be understood that all elements of the second adjustable anchor assembly 200 are disposed within the bone 410 in FIGS. 27-30 and thus would not be outwardly visible. In at least some embodiments, the method may include rotating the knob 264 counterclockwise relative to the handle 260 to rotate the second inner member 230 relative to the second outer member 210 to axially translate the second inner member 230 within the second outer member 210 to release the first flexible member 180 and the second flexible member 190 relative to the second adjustable anchor assembly 200.

Figure 29:
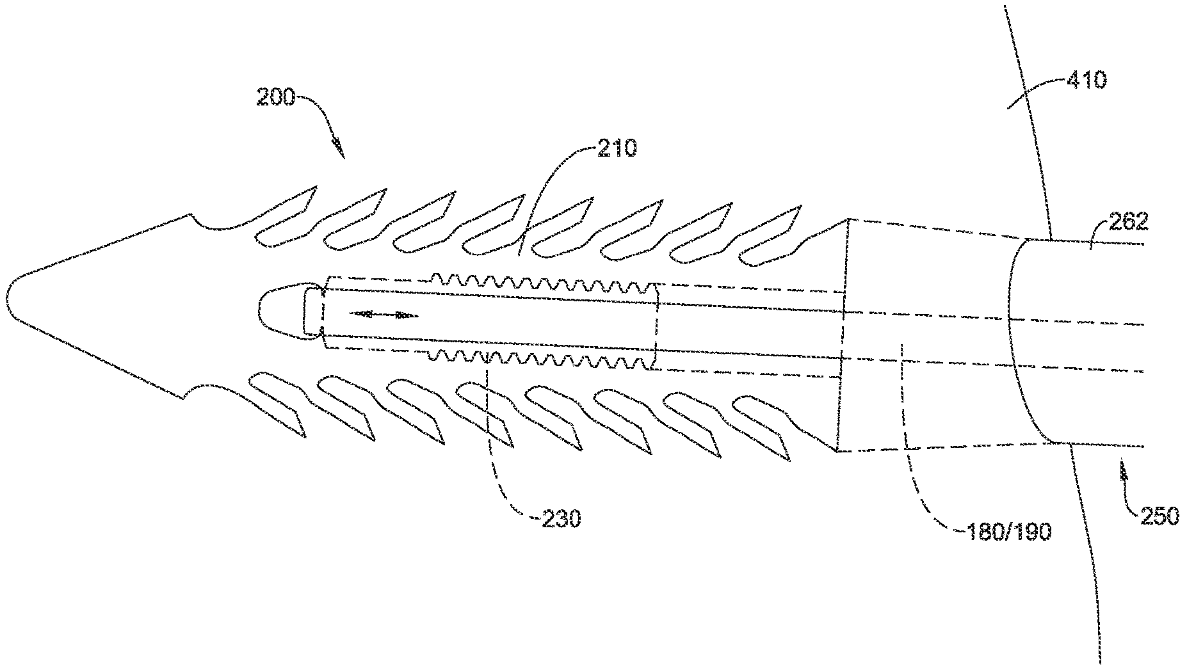

After releasing the first flexible member 180 and the second flexible member 190 relative to the second adjustable anchor assembly 200, the method may include adding tension to or releasing tension from the second free end 184 of the first flexible member 180 and/or adding tension to or releasing tension from the second free end 194 of the second flexible member 190, as seen in FIG. 29. In at least some embodiments, the second free end 184 of the first flexible member 180 and the second free end 194 of the second flexible member 190 may have tension added thereto or released therefrom individually and/or independently of each other.

Figure 30:
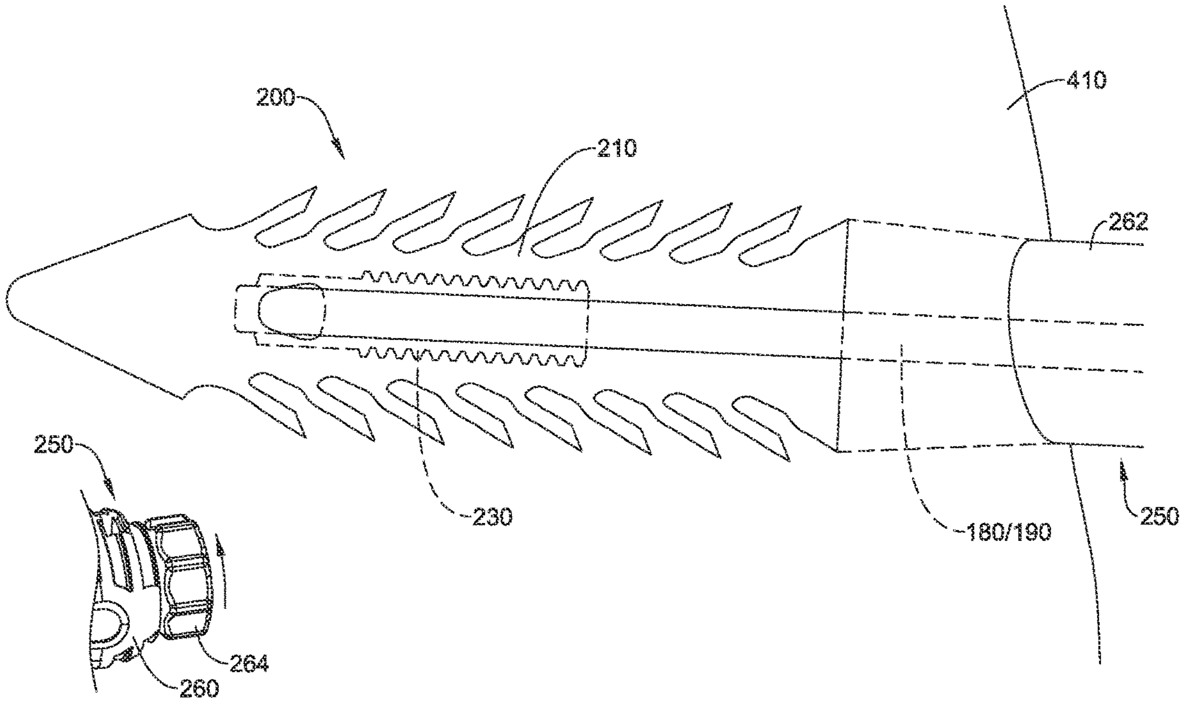

After adding tension to and/or releasing tension from the second free end 184 of the first flexible member 180 and the second free end 194 of the second flexible member 190, the method may include rotating the second inner member 230 of the second adjustable anchor assembly 200 relative to the second outer member 210 of the second adjustable anchor assembly 200 to axially translate the second inner member 230 within the second lumen 220 of the second outer member 210 to resecure the first flexible member 180 and the second flexible member 190 in position relative to the second adjustable anchor assembly 200, as seen in FIG. 30. The method may include rotating the knob 264 relative to the handle 260 to rotate the second inner member 230 relative to the second outer member 210 to axially translate the second inner member 230 within the second lumen 220 of the second outer member 210 to resecure the first flexible member 180 and the second flexible member 190 in position relative to the second adjustable anchor assembly 200, as shown in FIGS. 21-22. In at least some embodiments, the method may include rotating the knob 264 clockwise relative to the handle 260 to rotate the second inner member 230 relative to the second outer member 210 to axially translate the second inner member 230 within the second lumen 220 of the second outer member 210 to resecure the first flexible member 180 and the second flexible member 190 in position relative to the second adjustable anchor assembly 200.

Alternatively or additionally, in some embodiments, the method may include rotating the first inner member 230 relative to the first outer member 210 to release the first flexible member 180 and the second flexible member 190 relative to the first adjustable anchor assembly 200. The method may include rotating the knob 264 relative to the handle 260 to rotate the first inner member 230 relative to the first outer member 210 to axially translate the first inner member 230 within the first lumen 220 of the first outer member 210 to release the first flexible member 180 and the second flexible member 190 relative to the first adjustable anchor assembly 200, as shown in FIGS. 27-28. For clarity, elements of the first adjustable anchor assembly 200 that would be outwardly visible if not disposed within the bone 410 are shown in solid lines, while other elements are shown in phantom. However, it will be understood that all elements of the first adjustable anchor assembly 200 are disposed within the bone 410 in FIGS. 27-30 and thus would not be outwardly visible. In at least some embodiments, the method may include rotating the knob 264 counterclockwise relative to the handle 260 to rotate the first inner member 230 relative to the first outer member 210 to axially translate the first inner member 230 within the first lumen 220 of the first outer member 210 to release the first flexible member 180 and the second flexible member 190 relative to the first adjustable anchor assembly 200.

After releasing the first flexible member 180 and the second flexible member 190 relative to the first adjustable anchor assembly 200, the method may include adding tension to or releasing tension from the first free end 182 of the first flexible member 180 and/or adding tension to or releasing tension from the first free end 192 of the second flexible member 190, as seen in FIG. 29. In at least some embodiments, the first free end 182 of the first flexible member 180 and the first free end 192 of the second flexible member 190 may have tension added thereto or released therefrom individually and/or independently of each other.

After adding tension to the first free end 182 of the first flexible member 180 and the first free end 192 of the second flexible member 190, the method may include rotating the first inner member 230 of the first adjustable anchor assembly 200 relative to the first outer member 210 of the first adjustable anchor assembly 200 to axially translate the first inner member 230 within the first lumen 220 of the first outer member 210 to resecure the first flexible member 180 and the second flexible member 190 in position relative to the first adjustable anchor assembly 200, as seen in FIG. 30. The method may include rotating the knob 264 relative to the handle 260 to rotate the first inner member 230 relative to the first outer member 210 to axially translate the first inner member 230 within the first lumen 220 of the first outer member 210 to resecure the first flexible member 180 and the second flexible member 190 in position relative to the first adjustable anchor assembly 200, as shown in FIGS. 21-22. In at least some embodiments, the method may include rotating the knob 264 clockwise relative to the handle 260 to rotate the first inner member 230 relative to the first outer member 210 to axially translate the first inner member 230 within the first lumen 220 of the first outer member 210 to resecure the first flexible member 180 and the second flexible member 190 in position relative to the first adjustable anchor assembly 200.

Figure 31:
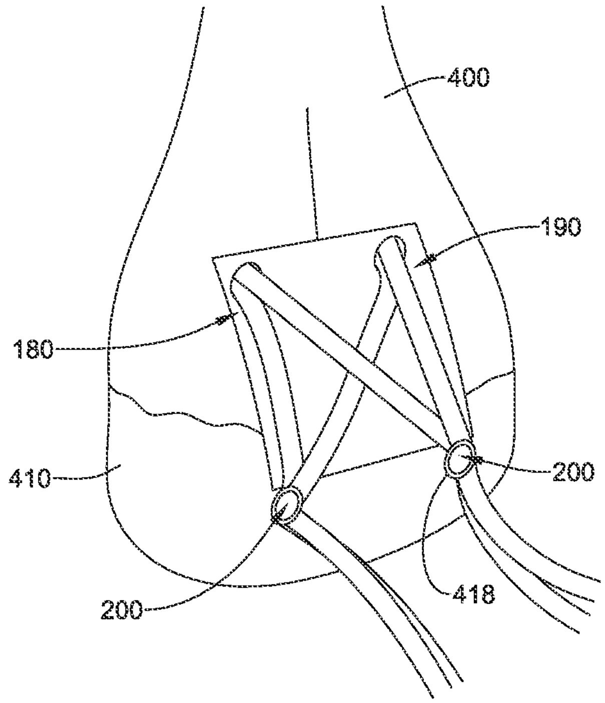
FIGS. 31-33 illustrate aspects of the method of reconstructing the Achilles tendon related to completion of the procedure.

After securing and/or resecuring the first flexible member 180 and the second flexible member 190 in position relative to the second adjustable anchor assembly 200, the shaft 262 and/or the second delivery device 250 may be disengaged from the second adjustable anchor assembly 200 by proximally retracting the shaft 262 and/or the second delivery device 250, without rotation, from the second adjustable anchor assembly 200, thereby leaving the second adjustable anchor assembly 200 secured within the fourth hole 418 formed in the bone 410, as seen in FIG. 31.

Figure 32:
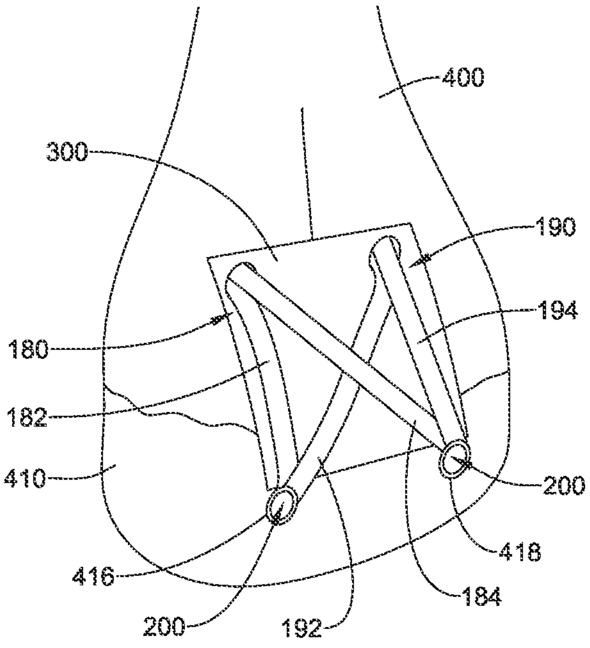

After satisfactorily securing and/or resecuring the first flexible member 180 and the second flexible member 190 in position relative to the first adjustable anchor assembly 200 and/or second adjustable anchor assembly 200, the first free end 182 of the first flexible member 180 and the first free end 192 of the second flexible member 190 may be trimmed to length at and/or adjacent the first adjustable anchor assembly 200, and the second free end 184 of the first flexible member 180 and the second free end 194 of the second flexible member 190 may be trimmed to length at and/or adjacent the second adjustable anchor assembly 200, as seen in FIG. 32.

In some embodiments, the collagen implant 300 may be held in position and/or may be held in contact with at least a portion of the Achilles tendon 400 by the first flexible member 180 and/or the second flexible member 190. In some embodiments, the first flexible member 180 may extend along, over, and/or generally parallel to a first lateral edge of the collagen implant 300. In some embodiments, the second flexible member 190 may extend along, over, and/or generally parallel to a second lateral edge of the collagen implant 300 opposite the first lateral edge of the collagen implant 300. In some embodiments, the first flexible member 180 and the second flexible member 190 may cooperate to form an X-shaped construct disposed between the first lateral edge of the collagen implant 300 and the second lateral edge of the collagen implant 300, the X-shaped construct being configured to secure at least a portion of the collagen implant 300 in position and/or in contact with at least a portion of the Achilles tendon 400. In some embodiments, the first flexible member 180 and/or the second flexible member 190 may be resorbable. In some embodiments, the first flexible member 180 and/or the second flexible member 190 may be non-resorbable.

Figure 33:
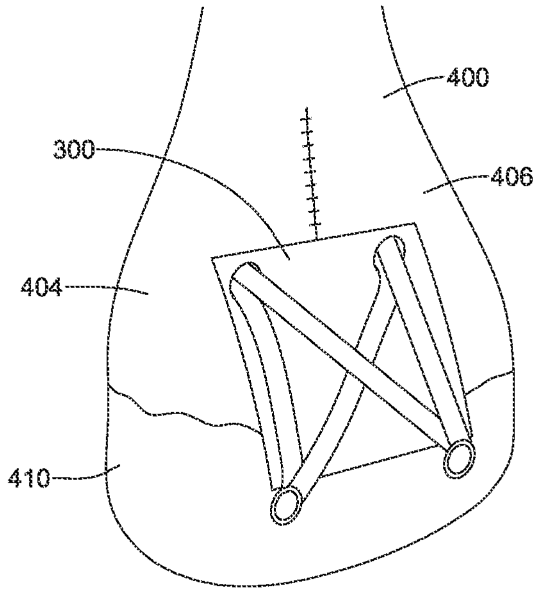

Finally, the method may include attaching the first lateral portion 404 of the Achilles tendon 400 to the second lateral portion 406 of the Achilles tendon 400 superiorly of the collagen implant 300, as seen in FIG. 33. In some embodiments, the first lateral portion 404 of the Achilles tendon 400 may be attached to the second lateral portion 406 of the Achilles tendon 400 using one or more sutures, staples, adhesives, combinations thereof, etc.

Figure 34:
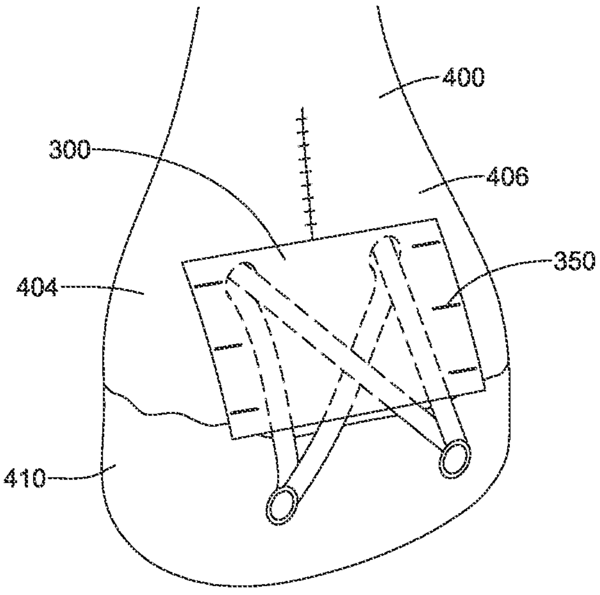
FIG. 34 illustrates aspects of an alternative configuration using the collagen implant of FIG. 4 in the method of reconstructing the Achilles tendon.

Alternatively or additionally, in some embodiments, the collagen implant 300 may be held in position and/or may be held in contact with at least a portion of the Achilles tendon 400 by one or more other attachment means such as, but not limited to, tendon staples 350, shown in FIG. 34, bone staples, absorbable suture, non-absorbable suture, adhesives, combinations thereof, etc. For example, the collagen implant 300 may be placed over a previously secured suture tape construct (e.g., first and second flexible members 180, 190) secured to a bone 410 with bone anchors as discussed above). Thus, the suture tape construct may be positioned between the collagen implant 300 and the first and second portions 404, 406 of the Achilles tendon 400. In other words, the first and second flexible members 180, 190 may be located underneath the collagen implant 300 without passing through the collagen implant 300. In some instances, the tendon staples 350 may be positioned laterally beyond the suture tape construct (e.g., the first and second flexible members 180, 190) through a portion of the collagen implant 300 extending laterally beyond the first and second flexible members 180, 190. In other instances, the tendon staples 350 may pass through portions of the first and second flexible members 180, 190 to secure the collagen implant 300 over the suture tape construct. Other configurations are also contemplated.

The various devices and/or elements described herein, including but not limited to the anchor member 100, the delivery device 150, the adjustable anchor assembly 200, the delivery device 250, the first flexible member 180, the second flexible member 190, etc., and individual elements or components thereof, may be made from suitable biocompatible materials including but not limited to polymeric materials, metallic materials, composite materials, etc. associated with medical devices. In some embodiments, the biocompatible materials may include one or more therapeutic agents and/or coatings disposed thereon and/or embedded therein.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A kit for reconstructing an Achilles tendon, comprising:
a first anchor member;
a first flexible member including:
a medial portion configured to engage the first anchor member, and
a first free end and a second free end opposite the medial portion and the first anchor member;
a second anchor member;
a second flexible member including:
a medial portion configured to engage the second anchor member, and
a first free end and a second free end opposite the medial portion and the second anchor member;
a first adjustable anchor assembly including a first outer member and a first inner member configured to axially translate within a first lumen of the first outer member in response to rotation of the first inner member relative to the first outer member;
a second adjustable anchor assembly including a second outer member and a second inner member configured to axially translate within a second lumen of the second outer member in response to rotation of the second inner member relative to the second outer member; and
a collagen implant configured to engage a surface of the Achilles tendon;
wherein the first anchor member and the second anchor member are separate anchor members, wherein the first flexible member and the second flexible member are separate flexible members, and wherein the medial portion of the first flexible member is configured to engage the first anchor member at a first engagement location and the medial portion of the second flexible member is configured to engage the second anchor member at a second engagement location spaced apart from the first engagement location; and
wherein the second free end of the first flexible member and the second free end of the second flexible member are configured to engage the second adjustable anchor assembly.

2. The kit of claim 1, wherein the first inner member is threadably engaged with the first outer member.

3. The kit of claim 1, wherein the first inner member is configured to axially translate in a distal direction within the first lumen of the first outer member to lock the first free end of the first flexible member and the first free end of the second flexible member in position relative to the first adjustable anchor assembly in response to clockwise rotation of the first inner member relative to the first outer member.

4. The kit of claim 1, wherein the second inner member is threadably engaged with the second outer member.

5. The kit of claim 1, wherein the second inner member is configured to axially translate in a distal direction within the second lumen of the second outer member to lock the second free end of the first flexible member and the second free end of the second flexible member in position relative to the second adjustable anchor assembly in response to clockwise rotation of the second inner member relative to the second outer member.

6. The kit of claim 1, wherein the first flexible member and the second flexible member are suture tapes.

* * * * *